US012758967B2

(12) United States Patent
McCully et al.

(10) Patent No.: US 12,758,967 B2
(45) Date of Patent: *Oct. 13, 2026

(54) PRODUCTS AND METHODS TO ISOLATE MITOCHONDRIA

(71) Applicants: Children's Medical Center Corporation, Boston, MA (US); Beth Israel Deaconess Medical Center, Inc., Boston, MA (US)

(72) Inventors: James D. McCully, Marblehead, MA (US); Douglas B. Cowan, West Roxbury, MA (US); Christina A. Pacak, Brookline, MA (US); Sidney Levitsky, Boston, MA (US)

(73) Assignees: Children's Medical Center Corporation, Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,655

(22) Filed: Oct. 5, 2022

(65) Prior Publication Data

US 2023/0219081 A1 Jul. 13, 2023

Related U.S. Application Data

(63) Continuation of application No. 15/318,557, filed as application No. PCT/US2015/035584 on Jun. 12, 2015, now Pat. No. 11,491,480.

(60) Provisional application No. 62/012,045, filed on Jun. 13, 2014.

(51) Int. Cl.
*B01L 3/00* (2006.01)
*C12M 1/00* (2006.01)
*G01N 1/40* (2006.01)

(52) U.S. Cl.
CPC ........... *B01L 3/5021* (2013.01); *C12M 47/06* (2013.01); *G01N 1/4077* (2013.01); *B01L 2200/0631* (2013.01); *B01L 2300/0681* (2013.01); *G01N 2001/4088* (2013.01)

(58) Field of Classification Search
None
See application file for complete search history.

(56) References Cited

U.S. PATENT DOCUMENTS

| | | | | |
|---|---|---|---|---|
| 2,561,043 | A | 7/1951 | Ayers | |
| 2,854,143 | A * | 9/1958 | Novak | B01L 3/5021 210/473 |
| 3,826,255 | A | 7/1974 | Diedrich et al. | |
| 4,046,146 | A | 9/1977 | Rosskamp et al. | |
| 4,253,468 | A | 3/1981 | Lehmbeck | |
| 4,268,460 | A | 5/1981 | Boiarski et al. | |
| 4,279,890 | A | 7/1981 | Harris et al. | |
| 4,510,829 | A | 4/1985 | Kintzel et al. | |
| 4,649,911 | A | 3/1987 | Knight et al. | |
| 5,460,940 | A | 10/1995 | Yves et al. | |
| 5,830,445 | A | 11/1998 | Bouillon et al. | |
| 6,468,798 | B1 | 10/2002 | Debs et al. | |
| 6,562,864 | B1 | 5/2003 | Larson | |
| 6,693,086 | B1 | 2/2004 | Dow et al. | |
| 6,695,227 | B1 | 2/2004 | Hayashi et al. | |
| 6,777,227 | B2 | 8/2004 | Ricci et al. | |
| 6,867,197 | B1 | 3/2005 | Davis et al. | |
| 7,125,434 | B2 | 10/2006 | Yavorsky et al. | |
| 7,279,326 | B2 | 10/2007 | Weissig et al. | |
| 7,431,222 | B2 | 10/2008 | Monterrosa | |
| 7,718,620 | B2 | 5/2010 | Szeto et al. | |
| 7,745,651 | B2 | 6/2010 | Heyes et al. | |
| 7,799,565 | B2 | 9/2010 | MacLachlan et al. | |
| 7,803,397 | B2 | 9/2010 | Heyes et al. | |
| 7,838,658 | B2 | 11/2010 | MacLachlan et al. | |
| 7,901,708 | B2 | 3/2011 | MacLachlan et al. | |
| 7,915,399 | B2 | 3/2011 | MacLachlan et al. | |
| 7,923,984 | B2 | 4/2011 | Philbert | |
| 7,982,027 | B2 | 7/2011 | MacLachlan et al. | |
| 8,058,069 | B2 | 11/2011 | Yaworski et al. | |
| 8,084,599 | B2 | 12/2011 | Rossi et al. | |
| 8,101,741 | B2 | 1/2012 | MacLachlan et al. | |
| 8,188,263 | B2 | 5/2012 | MacLachlan et al. | |
| 8,236,943 | B2 | 8/2012 | Lee et al. | |
| 8,283,333 | B2 | 10/2012 | Yaworski et al. | |
| 8,349,809 | B2 | 1/2013 | Brown | |
| 8,513,207 | B2 | 8/2013 | Brown | |
| 8,616,195 | B2 | 12/2013 | Power et al. | |

(Continued)

FOREIGN PATENT DOCUMENTS

| | | |
|---|---|---|
| AU | 2001013622 | 7/2001 |
| CA | 3049099 | 5/2018 |

(Continued)

OTHER PUBLICATIONS

Millar, A. H. et al. Isolation and Sub-fractionation of Mitochondria from Plants. Methods in Cell Biology. Jan. 1, 2001. 65: pp. 53-74. (Year: 2001).*

(Continued)

*Primary Examiner* — Nghi V Nguyen

(74) *Attorney, Agent, or Firm* — Fish & Richardson P.C.

(57) ABSTRACT

Filtration apparatuses, kits, and methods for rapid isolation of intact, viable mitochondria from tissues are described with mitochondria isolated by differential filtration through nylon mesh filters. Mitochondria can be isolated in less than 30 minutes using the filtration apparatuses, kits, and methods described.

7 Claims, 5 Drawing Sheets

(56) References Cited

U.S. PATENT DOCUMENTS

| | | | |
|---|---|---|---|
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,315,773 | B2 | 4/2016 | Schiedner et al. |
| 10,370,458 | B2 | 8/2019 | McCully et al. |
| 11,491,480 | B2 | 11/2022 | McCully et al. |
| 2001/0047966 | A1* | 12/2001 | Colpan ............. C12N 15/1017 210/808 |
| 2002/0046410 | A1 | 4/2002 | Lanza et al. |
| 2004/0131641 | A1 | 7/2004 | Mikszta et al. |
| 2004/0161421 | A1 | 8/2004 | Komowski et al. |
| 2004/0192595 | A1 | 9/2004 | Murakami et al. |
| 2005/0224608 | A1 | 10/2005 | Khan et al. |
| 2007/0015777 | A1 | 1/2007 | Bush et al. |
| 2007/0128726 | A1 | 6/2007 | Koob et al. |
| 2008/0014144 | A1 | 1/2008 | Saltzman et al. |
| 2008/0260637 | A1 | 10/2008 | Dickman |
| 2008/0275005 | A1 | 11/2008 | Murphy |
| 2009/0202606 | A1 | 8/2009 | Kim et al. |
| 2011/0008310 | A1 | 1/2011 | Cataldo et al. |
| 2011/0130309 | A1 | 6/2011 | Cardone |
| 2011/0177051 | A1 | 7/2011 | Galski-Lorberboum |
| 2011/0313143 | A1 | 12/2011 | Martin et al. |
| 2011/0321200 | A1 | 12/2011 | Hyde et al. |
| 2012/0039810 | A1 | 2/2012 | Gorenstein et al. |
| 2012/0107285 | A1 | 5/2012 | Hyde et al. |
| 2012/0107937 | A1 | 5/2012 | Hyde et al. |
| 2012/0110683 | A1 | 5/2012 | Shomura et al. |
| 2012/0171716 | A1 | 7/2012 | Sun et al. |
| 2013/0022666 | A1 | 1/2013 | Brzezinska |
| 2013/0149778 | A1 | 6/2013 | Chang et al. |
| 2013/0217114 | A1 | 8/2013 | Yan et al. |
| 2014/0051174 | A1 | 2/2014 | Burke et al. |
| 2014/0086886 | A1 | 3/2014 | Westenfelder |
| 2014/0106004 | A1 | 4/2014 | Wong et al. |
| 2014/0178993 | A1 | 6/2014 | Chang et al. |
| 2014/0193511 | A1 | 7/2014 | Yivgi-Ohana et al. |
| 2014/0314879 | A1 | 10/2014 | Lawendy et al. |
| 2015/0026833 | A1 | 1/2015 | Ande et al. |
| 2015/0079193 | A1 | 3/2015 | Yivgi-Ohana et al. |
| 2015/0344912 | A1 | 12/2015 | Kim et al. |
| 2016/0138008 | A1 | 5/2016 | Doudna et al. |
| 2016/0208243 | A1 | 7/2016 | Zhang et al. |
| 2017/0120237 | A1 | 5/2017 | McCully et al. |
| 2017/0151287 | A1 | 6/2017 | Von Maltzahn et al. |
| 2017/0290763 | A1 | 10/2017 | Su |
| 2018/0057610 | A1 | 3/2018 | McCully et al. |
| 2018/0340022 | A1 | 11/2018 | Lee |
| 2020/0123273 | A1 | 4/2020 | McCully et al. |
| 2022/0160782 | A1 | 5/2022 | McCully |
| 2022/0347212 | A1 | 11/2022 | McCully |
| 2022/0395531 | A1 | 12/2022 | McCully et al. |
| 2023/0183380 | A1 | 6/2023 | McCully et al. |
| 2023/0416413 | A1 | 12/2023 | McCully et al. |

FOREIGN PATENT DOCUMENTS

| | | |
|---|---|---|
| CN | 1187196 | 7/1998 |
| CN | 1662548 | 8/2005 |
| CN | 1832763 | 9/2006 |
| CN | 101146826 | 3/2008 |
| CN | 101693884 | 4/2010 |
| CN | 104662011 | 5/2015 |
| CN | 102791616 | 7/2015 |
| CN | 107249600 | 10/2017 |
| EP | 1766035 | 3/2007 |
| EP | 1781593 | 5/2007 |
| EP | 1519714 | 10/2010 |
| EP | 1664316 | 8/2012 |
| EP | 3402490 | 11/2018 |
| WO | WO 2006/059329 | 6/2006 |
| WO | WO 2008/137035 | 11/2008 |
| WO | WO 2008/152626 | 12/2008 |
| WO | WO 2012/085833 | 6/2012 |
| WO | WO 2013/035101 | 3/2013 |
| WO | WO 2013/171752 | 11/2013 |
| WO | WO 2014/113638 | 7/2014 |
| WO | WO 2015/192020 | 12/2015 |
| WO | WO 2016/135723 | 9/2016 |
| WO | WO 2017/095940 | 6/2017 |
| WO | WO 2017/095944 | 6/2017 |
| WO | WO 2017/095946 | 6/2017 |
| WO | WO 2017/124037 | 7/2017 |
| WO | WO 2020/214644 | 10/2020 |

OTHER PUBLICATIONS

Facundo, Heberty et al. Mitochondrial ATP-sensitive K+ channels are redox-sensitive pathways that control reactive oxygen species production. ScienceDirect, Apr. 1, 2007, 42(7). pp. 1039-1048. (Year: 2007).*

Ahmad et al., "Mirol regulates intercellular mitochondrial transport & enhances mesenchymal stem cell rescue efficacy," The EMBO Journal, May 2, 2014, 33(9):994-1010.

Akurathi et al., "Preliminary Evaluation of 18F-Rhodamine 6G as a Tumor-Imaging Agent," J Nucl Med, May 2013, 54 (Supplement 2): 1148, 2 pages.

Alfonzo et al., "Mitochondrial tRNA import-the challenge to understand has just begun." Biol. Chem, Jun. 2009, 390(8):717-722.

Allen et al., Angiopellosis as an Alternative Mechanism of Cell Extravasation, Stem Cells, Jan. 2017, 35:170-180.

Altschul et al "Basic Local Alignment Search Tool," Journal of molecular biology, Oct. 5, 1990, 215(3):403-10.

Angsutararux et al., "Chemotherapy-Induced Cardiotoxicity: Overview of the Roles of Oxidative Stress," Oxid Med Cell Longev, Oct. 2015, 795602, 13 pages.

Arora et al., "Cell Culture Media: A Review" Mater Methods, Sep. 2013, 3(175):24, 1-21.

AU Office Action in Australian Application No. 2017208013, dated Nov. 16, 2021, 7 pages.

AU Office Action in Australian Application No. 2021201217, dated Feb. 1, 2022, 5 pages.

AU Office Action in Australian Appln. No. 2015274367, dated Oct. 8, 2020, 5 pages.

Augustin et al., "Characterization of peptides released from mitochondria: evidence for constant proteolysis and peptide efflux," Journal of Biological Chemistry, Jan. 28, 2005, 280(4):2691-9.

Bacman et al., "Specific elimination of mutant mitochondrial genomes in patient-derived cells by mitoTALENs," Nature Medicine, Sep. 2013, 19(9):1111-3.

Bansal et al., "Photocontrolled nanoparticle delivery systems for biomedical applications," Accounts of Chemical Research, Oct. 2014, 47(10), 3052-3060.

Barhoumi et al., "Ultraviolet light-mediated drug delivery: Principles, applications, and challenges," Journal of Controlled Release, Dec. 2015, 219, 40 pages.

Bartel, "MicroRNAs: Genomics, Biogenesis, Mechanism, and Function," Cell, Jan. 23, 2004, 116:281-97.

Bartholomä et al., "18F-labeled rhodamines as potential myocardial perfusion agents: comparison of pharmacokinetic properties of several rhodamines," Nuclear Medicine and Biology, Oct. 1, 2015, 42(10):796-803.

Bartholomä et al., "Biological characterization of F18-labeled Rhodamine B, a potential positron emission tomography perfusion tracer," Nuclear Medicine and Biology, Nov. 1, 2013, 40(8):1043-8.

Bensley et al., "Studies on cell structure by the freezing-drying method VI. The preparation and properties of mitochondria," Anat Rec, Nov. 1934, 60:449-455.

(56) References Cited

OTHER PUBLICATIONS

Bershteyn et al., "Polymer-supported lipid shells, onions, and flowers," Soft Matter, Jan. 2008, 4(9):1787-91.
Birch-Machin et al., "An Evaluation of the Measurement of the Activities of Complexes I-IV in the Respiratory Chain of Human Skeletal Muscle Mitochondria," Biochemical Medicine and Metabolic Biology, 51:35-42, Feb. 1994, 35-42.
Birsoy et al., "An Essential Role of the Mitochondrial Electron Transport Chain in Cell Proliferation is to Enable Aspartate Synthesis," Cell, Jul. 2015, 162: 540-551.
Black et al., "Microarray and proteomic analysis of the cardioprotective effects of cold blood cardioplegia in the mature and aged male and female," Physiological Genomics, Nov. 1, 2012, 44(21):1027-41.
Boezeman et al., "Systematic review of clinical applications of monitoring muscle tissue oxygenation with near-infrared spectroscopy in vascular disease," Microvasc Res, Mar. 2016, 104, 47 pages.
Boldogh et al., "Cell-Free Assays for Mitochondria-Cytoskeleton Interactions," Methods in Cell Biology, Jan. 1, 2007, 80:683-706.
Bolender et al., "Multiple pathways for sorting mitochondrial precursor proteins," EMBO Reports, Jan. 2008, 9(1):42-9.
Boudreau et al. (2014). Platelets release mitochondria serving as substrate for bactericidal group IIA-secreted phospholipase A2 to promote inflammation. Blood 124(14): 2173-2183.
Brown et al., "Mitochondrial function as a therapeutic target in heart failure," Nature Reviews Cardiology, Apr. 2017, 14(4):238-50.
CA Office Action in Canadian Appln. No. 2,952,121, dated Aug. 9, 2021, 4 pages.
Calvo et al., "MitoCarta2. 0: an updated inventory of mammalian mitochondrial proteins," Nucleic Acids Research, Jan. 4, 2016, 44(D1):D1251-7.
Cameron et al., "Development of therapeutics that induce mitochondrial biogenesis for the treatment of acute and chronic degenerative diseases," Journal of Medicinal Chemistry, Dec. 8, 2016, 59(23):10411-34.
Cannon et al., "Brown Adipose Tissue: Function and Physiological Significance," Physiol Rev, Jan. 2004, 84: 277-359.
Cavers et al., "Chondriosomes (mitochondria) and their significance," New Phytologist, Mar. 1, 1914, 13(3):96-106.
Cedikova et al., "Mitochondria in white, brown, and beige adipocytes," Stem cells international, 2016:1-11, Jan. 2016.
Cell Biology A Laboratory Handbook, 3rd ed., Fernandez-Vizaeea et al., Nov. 2005, Chapter 10, 12 Pages.
Chance et al., "A simple and rapid assay of oxidative phosphorylation," Nature, Jun. 1955, 175(4469):1120-1.
Chance, "The interaction of energy and electron transfer reactions in mitochondria: II. General properties of adenosine triphosphate-linked oxidation of cytochrome and reduction of pyridine nucleotide," Journal of Biological Chemistry, May 1, 1961, 236(5):1544-54.
Chang et al., "Treatment of human cells derived from MERRF syndrome by peptide-mediated mitochondrial delivery," Cytotherapy, Dec. 1, 2013, 15(12):1580-96.
Chattopadhyay et al., "T3 fails to restore mitochondrial thiol redox status altered by experimental hypothyroidism in rat testis," General and Comparative Endocrinology, Oct. 1, 2010, 169(1):39-47.
Chen et al., "Absolute quantification of matrix metabolites reveals the dynamics of mitochondrial metabolism," Cell, Aug. 2016, 166(5):1324-37.
Cheng et al., "Brief report: Mechanism of extravasation of infused stem cells," Stem Cells, 2012, 30: 2835-2842.
Choi et al., "Cardiac conduction through engineered tissue," The American Journal of Pathology, Jul. 1, 2006, 169(1):72-85.
Claude, "Fractionation of Mammalian Liver Cells by Differential Centrifugation," J Exp Med, Apr. 1946, 84:61-89.
CN Office Action in Chinese Application No. 201580039651.4, dated Jul. 4, 2018, 9 pages (English translation).
CN Office Action in Chinese Application No. 201580039651.4, dated May 5, 2019, 9 pages (English translation).
CN Office Action in Chinese Appln. No. 201580039651.4, dated Aug. 17, 2020, 37 pages (with English translation).
CN Office Action in Chinese Appln. No. 201580039651.4, dated Jan. 21, 2021, 10 pages (with English translation).
CN Office Action in Chinese Appln. No. 201780013452.5, dated Nov. 19, 2021, 10 pages (with English translation).
Colman, "Effects of amino acid sequence changes on antibody-antigen interactions," Research in Immunology, Jan. 1, 1994, 145(1):33-6.
Cong et al., "Multiplex genome engineering using CRISPR/Cas systems," Science, Feb. 15, 2013, 339(6121):819-23.
Cowan et al., "Intracoronary delivery of mitochondria to the ischemic heart for cardioprotection." PloS one, Aug. 2016, 11(8): e0160889, 19 pages.
Cramer et al., "Methods for mycelial breakage and isolation of mitochondria and vacuoles of neurospora," Analytical Biochemistry, Feb. 1983, 128: 384-392.
Cypess et al., "Brown fat as a therapy for obesity and diabetes." Current Opinion in Endocrinology, Diabetes, and Obesity, Apr. 2010, 17: 143-149.
Dare et al., "The mitochondria-targeted anti-oxidant MitoQ decreases ischemia-reperfusion injury in a murine syngeneic heart transplant model," J Heart Lung Transplant, Nov. 2015, 34(11):1471-80.
Doench et al., "siRNAs can function as miRNAs," Genes & Development, Feb. 15, 2003, 17(4):438-42.
Doenst et al., "Cardiac metabolism in heart failure: implications beyond ATP production," Circulation Research., Aug. 30, 2013, 113(6):709-24.
Dolezal et al., "Evolution of the molecular machines for protein import into mitochondria," Science, Jul. 21, 2006, 313(5785):314-8.
Doulamis et al., "Mitochondrial transplantation for myocardial protection in diabetic hearts," European Journal of Cardio-Thoracic Surgery, May 1, 2020, 57(5):836-45.
Ejsing et al., "Global analysis of the yeast lipidome by quantitative shotgun mass spectrometry," Proceedings of the National Academy of Sciences, Feb. 17, 2009, 106(7):2136-41.
Elliott et al., "Mitochondria organelle transplantation: introduction of normal epithelial mitochondria into human cancer cells inhibits proliferation and increases drug sensitivity," Breast Cancer Res. Treat., 2012, 136:347-354.
Emani et al., "Autologous mitochondrial transplantation for dysfunction after ischemia-reperfusion injury," The Journal of Thoracic and Cardiovascular Surgery, Jul. 1, 2017, 154(1):286-9.
EP European Search Report in European Appln. No. 20155650.3, dated Aug. 13, 2020, 15 pages.
EP European Search Report in European Appln. No. 20155650.3, dated Sep. 21, 2020, 17 pages.
EP European Search Report in European Appln. No. 20790601.7, dated Jul. 17, 2022, 12 pages.
EP Extended European Search Report in European Application No. 17739105.9 dated Jul. 8, 2019, 10 pages.
EP Extended European Search Report in European Appln. No. 20155650.3, dated Jan. 12, 2021, 14 pages.
EP Extended European Search Report issued in European Patent Application No. 16871432.7, dated Jun. 4, 2019, 8 pages.
EP Extended European Search Report issued in European Patent Application No. 16871436.8, dated Jun. 4, 2019, 7 pages.
EP Office Action by European Appln. No. 20155650.3, dated Dec. 15, 2021, 5 pages.
EP Office Action in European Application No. 15733576.1, dated May 3, 2018, 5 pages.
EP Partial Supplementary European Search Report issued in European Patent Application No. 16871434.3, dated Jun. 4, 2019, 12 pages.
Ernster et al., "Mitochondria: a historical review," The Journal of Cell Biology, Dec. 1981, 91(3):227s-55s.
Facundo et al., "Mitochondrial ATP-sensitive K+ channels are redox-sensitive pathways that control reactive oxygen species production," ScienceDirect, Apr. 1, 2007, 42(7):1039-1048.
Faulk et al., "Magnesium cardioplegia enhances mRNA levels and the maximal velocity of cytochrome oxidase I in the senescent myocardium during global ischemia," Circulation, Nov. 1, 1995, 92(9):405-12.

(56) References Cited

OTHER PUBLICATIONS

Faulk et al., "Myocardial mitochondrial calcium accumulation modulates nuclear calcium accumulation and DNA fragmentation," The Annals of thoracic surgery, Aug. 1, 1995, 60(2):338-44.
Feng et al., "Isolation and Observation of Mitochondrion," Experimental Instructions for Cell Biology and Cell Engineering Experiments, Human Science and Technology Press, Aug. 1, 2013, 39-41, 10 pages (English translation of the relevant portion is provided).
Fernández-Vizarra et al., "Tissue-specific differences in mitochondrial activity and biogenesis," Mitochondrion, Jan. 1, 2011, 11(1):207-13.
Fernandez-Vizarra et al., "Isolation of mitochondria for biogenetical studies: An update," Mitochondrion, Apr. 2010, 10:253-262.
Finkel et al., "The ins and outs of mitochondrial calcium," Circulation Research, May 22, 2015, 116(11):1810-9.
Flaquer et al., "Mitochondrial genetic variants identified to be associated with posttraumatic stress disorder," Translational Psychiatry, Mar. 2015, 5(3):e524, 7 pages.
Frezza et al., "Organelle isolation: functional mitochondria from mouse liver, muscle and cultured fibroblasts," Nature Protocols, 2007, 2(2): 287-295.
Friehs et al., "Pressure-overload hypertrophy of the developing heart reveals activation of divergent gene and protein pathways in the left and right ventricular myocardium," American Journal of Physiology—Heart and Circulatory Physiology, Mar. 1, 2013, 304(5):H697-708.
Gabriel et al., "The mitochondrial machinery for import of precursor proteins," Protein Targeting Protocols, Jan. 2007, 390, 99-117.
Geng et al., "Microfluidic electroporation for cellular analysis and delivery," Lab on a Chip, 2013, 13(19):3803-21.
Glancy et al., "Effect of calcium on the oxidative phosphorylation cascade in skeletal muscle mitochondria," Biochemistry, Apr. 23, 2013, 52(16):2793-809.
Gostimskaya et al., "Preparation of highly coupled rat heart mitochondria," Sep. 2010, J Vis Exp, 43: e2202, 4 pages.
Graham et al., "Isolation of Mitochondria from Tissues and UNIT 3.3 Cells by Differential Centrifugation," Current Protocol in Cell Biology, May 2001, 3(3.3), 15 pages.
Graham et al., "Isolation of nuclei and nuclear membranes from animal tissues," Current Protocols in Cell Biology, Oct. 2001, 12(1):3-10.
Gram et al., "Skeletal muscle mitochondrial H2O2 emission increases with immobilization and decreases after aerobic training in young and older men," The Journal of Physiology, Sep. 1, 2015, 593(17):4011-27.
Green et al., "Metabolic, enzymatic, and transporter responses in human muscle during three consecutive days of exercise and recovery," American Journal of Physiology—Regulatory, Integrative and Comparative Physiology, Oct. 2008, 295(4):R1238-50.
Grieve et al., "Microvascular obstruction by intracoronary delivery of mesenchymal stem cells and quantification of resulting myocardial infarction by cardiac magnetic resonance," Circulation: Heart Failure, May 2010, 3(3):e5-6, 3 pages.
Gross et al., "Isolation of functional mitochondria from rat kidney and skeletal muscle without manual homogenization," Anal Biochem, Nov. 2011, 418:213-223.
Guo et al., "Cardiovascular toxicities from systemic breast cancer therapy," Front Oncol, Dec. 4, 2014, 10 pages.
Hamilton, "The Mitochondria Mystery: Hidden risks for 'three-person' babies," Nature, Sep. 2015, 525(7570):444-6.
Han et al., "An unexpectedly labile mitochondrially encoded protein is required for Mta expression," Immunogenetics, Jul. 1989, 29: 258-264.
Hao et al., "Hydroxytyrosol promotes mitochondrial biogenesis and mitochondrial function in 3T3-L1 adipocytes," The Journal of Nutritional Biochemistry, Jul. 1, 2010, 21(7):634-44.
Harms et al., "Brown and beige fat: development, function and therapeutic potential," Nature Medicine, Oct. 2013, 19: 1252-1263.
Hartwig et al., "A critical comparison between two classical and a kit-based method for mitochondria isolation," Proteomics, Jun. 2009, 9(11):3209-14.
Hendel et al., "Chemically modified guide RNAs enhance CRISPR-Cas genome editing in human primary cells," Nature Biotechnology, Sep. 2015, 33(9):985-9.
Herzog et al., "A novel informatics concept for high-throughput shotgun lipidomics based on the molecular fragmentation query language," Genome Biology, Jan. 2011, 12(1):1-25.
Herzog et al., "LipidXplorer: a software for consensual cross-platform lipidomics," PLoS One, PloS one, Jan. 17, 2012, 7(1):e29851, 7 pages.
Hoeper et al., "Mortality in pulmonary arterial hypertension: prediction by the 2015 European pulmonary hypertension guidelines risk stratification model," European Respiratory Journal, Aug. 1, 2017, 50(2), 10 pages.
Hogeboom et al., "Cytochemical studies of mammalian tissues; isolation of intact mitochondria from rat liver; some biochemical properties of mitochondria and submicroscopic particulate material," J Biol Chem, Feb. 1948, 172:619-635.
Ikon et al., "Exogenous cardiolipin localizes to mitochondria and prevents TAZ knockdown-induced apoptosis in myeloid progenitor cells," Biochem Biophys Res Commun, Aug. 2015, 464(2):580-5.
Islam et al., "Mitochondrial transfer from bone-marrow-derived stromal cells to pulmonary alveoli protects against acute lung injury," Nature Medicine, May 2012, 18: 759-765.
Jo et al., "Efficient mitochondrial genome editing by CRISPR/Cas9," BioMed Research International, Oct. 2015, vol. 2015.
JP Japanese Office Action in Japanese Appln. No. 2017-517221, dated Dec. 22, 2022, 6 pages (with English translation).
JP Japanese Office Action in Japanese Appln. No. 2018-536875, dated Dec. 27, 2021, 15 pages (with English translation).
JP Japanese Office Action in Japanese Appln. No. 2020-173126, dated Nov. 1, 2022, 5 pages (with English translation).
JP Office Action in Japanese Appln. No. 2017-517221, dated Mar. 19, 2019, 4 pages.
JP Office Action in Japanese Appln. No. 36443-0031002, dated Jan. 27, 2021, 22 pages (with English translation).
Kalogeris et al., "Cell biology of ischemia/reperfusion injury. International review of cell and molecular biology," Jan. 1, 2012, 298:229-317.
Kassab et al., "Morphometry of pig coronary arterial trees," American Journal of Physiology—Heart and Circulatory Physiology, Jul. 1, 1993, 265(1):H350-65.
Kaul et al., "Insulin resistance in type 1 diabetes mellitus," Metabolism, Dec. 2015, 64(12), 39 pages.
Kaza et al., "Myocardial rescue with autologous mitochondrial transplantation in a porcine model of ischemia/reperfusion," The Journal of Thoracic and Cardiovascular Surgery, Apr. 2017, 153(4), 934-943.
Keeney et al., "Mitochondrial gene therapy augments mitochondrial physiology in a Parkinson's disease cell model," Human Gene Therapy, Aug. 1, 2009, 20(8):897-907.
Kirby et al., "Biochemical assays of respiratory chain complex activity," Methods in Cell Biology, Jan. 1, 2007, 80:93-119.
Kishida et al., "Reprogrammed Functional Brown Adipocytes Ameliorate Insulin Resistance and Dyslipidemia in Diet-Induced Obesity and Type 2 Diabetes," Stem Cell Reports, Oct. 2015, 5(4):569-81.
Kitani et al., "Internalization of isolated functional mitochondria: involvement of micropinocytosis," Journal of Cellular and Molecular Medicine, Aug. 2014, 18(8):1694-703.
Kornfeld et al., "Mitochondrial reactive oxygen species at the heart of the matter: new therapeutic approaches for cardiovascular diseases," Circulation Research, May 22, 2015, 116(11):1783-99.
Kunze et al., "The similarity between N-terminal targeting signals for protein import into different organelles and its evolutionary relevance," Frontiers in Physiology, Sep. 24, 2015, 6:259, 27 pages.
Kusminski et al., "Mitochondrial dysfunction in white adipose tissue," Trends in endocrinology & metabolism, 23(9):435-43, Sep. 2012.
Lang et al., "Recommendations for cardiac chamber quantification by echocardiography in adults: an update from the American

(56) References Cited

OTHER PUBLICATIONS

Society of Echocardiography and the European Association of Cardiovascular Imaging," European Heart Journal-Cardiovascular Imaging, Mar. 1, 2015, 16(3):233-71.
Lau et al., "The 2015 ESC/ERS Guidelines for the diagnosis and treatment of pulmonary hypertension: a practical chronicle of progress," European Respiratory Journal, Oct. 1, 2015, 46(4):879-82.
Layland et al., "Adenosine: physiology, pharmacology, and clinical applications," JACC: Cardiovascular Interventions, Jun. 2014, 7(6):581-91.
Levitsky et al., "Mitochondrial DNA deletions in coronary artery bypass grafting patients," European Journal of Cardio-thoracic Surgery, Nov. 2003, 24: 777-784.
Lim et al., "Microarray analysis shows that some microRNAs downregulate large numbers of target mRNAs," Nature, Feb. 2005, 433(7027):769-73.
Lim et al., "Cold-induced activation of brown adipose tissue and adipose angiogenesis in mice," Nature Protocols, Mar. 2012, 7: 606-615.
Lim et al., "Levosimendan Reduces Mortality in Adults with Left Ventricular Dysfunction Undergoing Cardiac Surgery: A Systematic Review and Meta-analysis," J Card Surg, Jul. 2015, 30(7):547-54.
Lin et al "Incorporation of VSV-G produces fusogenic plasma membrane vesicles capable of efficient transfer of bioactive macromolecules and mitochondria" Biomed Microdevices (2016) 18: 41.
Lin et al., "Isolated mitochondria infusion mitigates ischemia-reperfusion injury of the liver in rats," Shock, Mar. 2013, 39: 304-310.
Lin et al., "Human white adipose tissue vasculature contains endothelial colony-forming cells with robust in vivo vasculogenic potential," Angiogenesis, Oct. 2013, 16(4): 735-744.
Liu et al., "Disrupted Renal Mitochondrial Homeostasis after Liver Transplantation in Rats," PLoS One, Oct. 2015, 10(10):e0140906.
Maniataki et al., "Human mitochondrial tRNAMet is exported to the cytoplasm and associates with the Argonaute 2 protein. RNA," Jun. 1, 2005, 11(6):849-52.
Masuzawa et al., "Transplantation of autologously derived mitochondria protects the heart from ischemia-reperfusion injury," Amer J Physiol Heart Circ Physiol, Apr. 2013, 304:H966-H982.
Matsuda et al., "Developmental Differences in Cytosolic Calcium Accumulation Associated With Global Ischemia Evidence for Differential Intracellular Calcium Channel Receptor Activity," Circulation, Nov. 1997, 96(9 Supp):II-233-9.
McCully et al., "Injection of isolated mitochondria during early reperfusion for cardioprotection," American Journal of Physiology—Heart and Circulatory Physiology, Jan. 2009, 296: H94-H105.
McCully et al., "Abstract 2272: Mitochondrial Transplantation for Cardioprotection," Circulation, Oct. 2007, 116: II, 2 pages.
McCully et al., "Mitochondrial transplantation for therapeutic use," Clin. Trans. Med., Dec. 2016, 5:16, 13 pages.
McCully et al., "Adenosine-enhanced ischemic preconditioning: adenosine receptor involvement during ischemia and reperfusion," Am J Heart Cir Physiol, Feb. 2001, 280: H591-H602.
McCully et al., "Age-and Gender-Related Differences in Mitochondrial Oxygen Consumption and Calcium With Cardioplegia and Diazoxide," Ann Thorac Surg, Mar. 2007, 83: 1102-9.
MCully et al., "Diazoxide Amelioration of Myocardial Injury and Mitochondrial Damage During Cardiac Surgery," Ann Thorac Surg, Dec. 2002, 74: 2138-46.
Melero-Martin et al., "In vivo vasculogenic potential of human blood-derived endothelial progenitor cells," Blood, Jun. 2007, 109(11), 4761-4768.
Mercer et al., "Operating characteristics of some compressed-air nebulizers," American Industrial Hygiene Association Journal, Jan. 1, 1968, 29(1):66-78.
Millar et al. "Isolation and subfractionation of mitochondria from plants," Methods in cell biology, Jan. 1, 2001, 65:53-74.
Moskowitzova et al., "Mitochondrial transplantation prolongs cold ischemia time in murine heart transplantation," The Journal of Heart and Lung Transplantation, Jan. 1, 2019, 38(1):92, 25 pages.
Mumtaz et al., "Design of liposomes for circumventing the reticuloendothelial cells," Glycobiol, Nov. 1991, 1 (5): 505-510.
Néchad et al., "Development of brown fat cells in monolayer culture: I. Morphological and biochemical distinction from white fat cells in culture," Experimental Cell Research, Nov. 1, 1983, 149(1):105-18.
Neubauer, "The failing heart-an engine out of fuel, " New England Journal of Medicine, Mar. 15, 2007, 356(11): 1140-51.
Nishikawa et al., "Nonviral vectors in the new millennium: delivery barriers in gene transfer," Human Gene Therapy, May 20, 2001, 12(8):861-70.
Noly et al., "Right ventricular mitochondrial respiratory function in a piglet model of chronic pulmonary hypertension," The Journal of Thoracic and Cardiovascular Surgery, Jan. 1, 2020, 159(1):129-40.
Novak et al., "Preparation of subcellular fractions suitable for biochemical analyses from human subcutaneous adipose tissue obtained by needle biopsy—I. Isolation of mitochondria on a microscale," Experimental Cell Research, Aug. 1972, 73: 335-344.
Novobrantseva et al., "Systemic RNAi-mediated gene silencing in nonhuman primate and rodent myeloid cells," Molecular Therapy-Nucleic Acids, Jan. 1, 2012, 1:e4, 13 pages.
O'Connell et al., "The effects of cryopreservation on sperm morphology, motility and mitchondrial function," Human Reproduction, Mar. 1, 2002, 17(3):704-9.
Olson et al., "Changes in endogenous substrates of isolated rabbit heart mitochondria during storage," Journal of Biological Chemistry, Jan. 25, 1967, 242(2):325-32.
Orive et al., "Cell encapsulation: technical and clinical advances," Trends in Pharmacological Sciences, Aug. 1, 2015, 36(8):537-46.
Orme-Johnson, "Appendix 2. Direct and indirect inhibitors of mitochondrial ATP synthesis," Methods in Cell Biology, 2007, 80:813-26.
Pacak et al., "Actin-dependent mitochondrial internalization in cardiomyocytes: evidence for rescue of mitochondrial function," Biology Open, Jul. 2015, 4: 622-626.
Pacak et al., "Superparamagnetic iron oxide nanoparticles function as a long-term, multi-modal imaging label for non-invasive tracking of implanted progenitor cells," PLoS One, Sep. 24, 2014, 9(9):e108695.
Pallotti et al., "Isolation and subfractionation of mitochondria from animal cells and tissue culture lines," Methods in Cell Biology, Jan. 1, 2001, 65:1-35.
PCT International Preliminary Report on Patentability in International Application No. PCT/US2017/013564, dated Jul. 17, 2018, 14 pages.
PCT International Preliminary Report on Patentability in International Appln. No. PCT/US2019/058924, dated Nov. 2, 2021, 11 pages.
PCT International Preliminary Report on Patentability in International Appln. No. PCT/US2020/018371, dated Aug. 10, 2021, 12 pages.
PCT International Preliminary Report on Patentability in International Appln. No. PCT/US2020/028219, dated Sep. 28, 2021, 10 pages.
PCT International Search Report and Written Opinion in International Application No. PCT/US2015/035584, dated Sep. 2, 2015, 12 pages.
PCT International Search Report and Written Opinion in International Application No. PCT/US2016/064238, dated Apr. 13, 2017, 13 pages.
PCT International Search Report and Written Opinion in International Application No. PCT/US2016/064247 dated May 10, 2017, 16 pages.
PCT International Search Report and Written Opinion in International Application No. PCT/US2016/064251 dated May 8, 2017, 15 pages.
PCT International Search Report and Written Opinion in International Application No. PCT/US2017/013564, dated Jun. 5, 2017, 12 pages.

(56) References Cited

OTHER PUBLICATIONS

PCT International Search Report and Written Opinion in International Appln. No. PCT/US2019/058924, dated Jan. 21, 2020, 17 pages.
PCT International Search Report and Written Opinion in International Appln. No. PCT/US2020/018371, dated May 7, 2020, 14 pages.
PCT International Search Report and Written Opinion in International Appln. No. PCT/US2020/028219, dated Jul. 15, 2020, 12 pages.
Peschechera et al., ""Browning" of adipose tissue-regulation and therapeutic perspectives," Archives of physiology and biochemistry, 119(4):151-60, Oct. 2013.
Pfanner et al., "Assembling the mitochondrial outer membrane," Nature Structural & Molecular Biology, Nov. 2004, 11(11):1044-8.
Phillips et al., "Homogenous protein programming in the mammalian left and right ventricle free walls," Physiological Genomics, Nov. 2011, 43(21):1198-206.
Phinney et al., "Mesenchymal stem cells use extracellular vesicles to outsource mitophagy and shuttle microRNAs," Nature Communications, Oct. 7, 2015, 6(1):1-5.
Pinton et al., "Biosensors for the detection of calcium and pH," Methods in Cell Biology, Jan. 1, 2007, 80:297-325.
Preble et al., "Quality Control Parameters for Mitochondria Transplant in Cardiac Tissue," Mol. Biol., Jun. 2, 2014, 2(1):1008.
Preble et al., "Rapid isolation and purification of mitochondria for transplantation by tissue dissociation and differential filtration," JoVE (Journal of Visualized Experiments), Sep. 6, 2014, (91):e51682, 6 pages.
Quirós et al., "New roles for mitochondrial proteases in health, ageing and disease," Nature Reviews Molecular Cell biology, Jun. 2015, 16(6):345-59.
Rahman et al., "Demarcating the membrane damage for the extraction of functional mitochondria," Microsystems & Nanoengineering, Dec. 31, 2018, 4(1):1-2.
Rajewsky, "microRNA target predictions in animals," Nature Genetics, Jun. 2006, 38(6):S8-13.
Ran et al., "Double nicking by RNA-guided CRISPR Cas9 for enhanced genome editing specificity," Cell, Sep. 12, 2013, 154(6):1380-9.
Ran et al., "Genome engineering using the CRISPR-Cas9 system," Nature Protocols, Nov. 2013, 8(11):2281-308.
Risum et al., "Variability of global left ventricular deformation analysis using vendor dependent and independent two-dimensional speckle-tracking software in adults," Journal of the American Society of Echocardiography, Nov. 1, 2012, 25(11):1195-203.
Rodiger et al., "Simultaneous isolation of intact mitochondria and chloroplasts from a single pulping of plant tissue," Journal of Plant Physiology, May 2010, 167: 620-624.
Rogers et al., "When Cells Become Organelle Donors," Physiology, Nov. 2013, 28: 414-422.
Rosner et al., "Merging high-quality biochemical fractionation with a refined flow cytometry approach to monitor nucleocytoplasmic protein expression throughout the unperturbed mammalian cell cycle," Nature Protocols, Mar. 2013, 8(3):602-26.
Roucou et al., "A cytochrome c-GFP fusion is not released from mitochondria into the cytoplasm upon expression of Bax in yeast cells," FEBS letters, Apr. 14, 2000, 471(2-3):235-9.
Rousou et al., "Opening of mitochondrial KATP channels enhances cardioprotection through the modulation of mitochondrial matrix volume calcium accumulation, and respiration," American Journal of Physiology—Heart and Circulatory Physiology, Nov. 2004, 287:H967-H976.
Rowley et al., "Meeting lot-size challenges of manufacturing adherent cells for therapy," Bioprocess Int, Mar. 2012, 10(3), 16-22.
Rubino et al., "HmtDB, a genomic resource for mitochondrion-based human variability studies," Nucleic Acids Research, Jan. 2012, 40(D1):D1150-9.
Rudikoff et al., Single amino acid substitution altering antigen-binding specificity,: Proceedings of the National Academy of Sciences, Mar. 1, 1982, 79(6):1979-83.
Rustom et al., "Nanotubular Highways for Intercellular Organelle Transport," Science, Feb. 2004, 303: 1007-1010.
Sampaio et al., "Membrane lipidome of an epithelial cell line," Proceedings of the National Academy of Sciences, Feb. 1, 2011, 108(5):1903-7.
Sass et al., "Folding of Fumarase during Mitochondrial Import Determines its Dual Targeting in Yeast," The Journal of Biological Chemistry, Nov. 2008, 278:45109-45116.
Shapiro et al., "Clearance and maintenance of blood nucleotide levels with adenosine triphosphate-magnesium chloride injection," Circulatory Shock, Jan. 1, 1992, 36(1):62-7.
Schmitt et al., "A semi-automated method for isolating functionally intact mitochondria from cultured cells and tissue biopsies," Anal Biochem, Dec. 2013, 443:66-74.
Seyfried, "Cancer as a mitochondrial metabolic disease," Frontiers in Cell and Developmental Biology, Jul. 2015, 3: 43 (12 pages).
Sharei et al., "A vector-free microfluidic platform for intracellular delivery," Proceedings of the National Academy of Sciences, Feb. 5, 2013, 110(6):2082-7.
Shin et al., "A novel biological strategy for myocardial protection by intracoronary delivery of mitochondria: safety and efficacy," JACC: Basic to Translational Science, Dec. 2019, 4(8):871-88.
Sieber et al., "A protein shuttle system to target RNA into mitochondria," Nucleic Acids Research, Aug. 1, 2011, 39(14):e96, 9 pages.
Sivitz et al., "Mitochondrial dysfunction in diabetes: from molecular mechanisms to functional significance and therapeutic opportunities," Antioxidants & Redox signaling, Feb. 15, 2010, 12(4):537-77.
Skrabanja et al., "Potential value of adenosine 5'-triphosphate (ATP) and adenosine in anaesthesia and intensive care medicine," British Journal of Anaesthesia, May 1, 2005, 94(5):556-62.
Slowinska et al., "Mitochondrial membrane potential and reactive oxygen species in liquid stored and cryopreserved turkey (*Meleagris gallopavo*) spermatozoa" Poultry Science, 97:3709-3717, 2018.
Soubannier et al., "A vesicular transport pathway shuttles cargo from mitochondria to lysosomes," Current Biology, Jan. 24, 2012, 22(2):135-41.
Spees et al., "Mitochondrial transfer between cells can rescue aerobic respiration," Proceedings of the National Academy of Sciences, Jan. 31, 2006, 103(5):1283-8.
Spinazzi et al., "Assessment of mitochondrial respiratory chain enzymatic activities on tissues and cultured cells," Nature Protocols, Jun. 2012, 7(6):1235-46.
Spuch et al., "Liposomes for targeted delivery of active agen+A3ts against neurodegenerative diseases (Alzheimer's disease and Parkinson's disease)," Journal of Drug Delivery, Jul. 13, 2011, vol. 2011, 13 pages.
Starkov et al., "Protein Misfolding and Cellular Stress in Disease and Aging," Measurement of Mitochondrial ROS Production, Jul. 7, 2010, 648:245-55.
Starkov, "Measurement of mitochondrial ROS production" Methods Mol Biol (2010) vol. 648, pp. 245-255.
Stephanopoulos et al., "Choosing an effective protein bioconjugation strategy," Nature Chemical Biology, Dec. 2011, 7: 876-884.
Stitt et al., "Metabolite Levels in Specific Cells and Subcellular Compartments of Plant Leaves," Methods in Enzymology, Jan. 1989, 174: 518-552.
Stojanovski et al., "Import of proteins into mitochondria," Methods in Cell Biology, Jan. 2007, 80:783-806.
Su et al., "Mitochondrial transplantation attenuates airway hyperresponsiveness by inhibition of cholinergic hyperactivity," Theranostics, May 2016;6(8):1244-60.
Sun et al. "Systemic combined melatonin-mitochondria treatment improves acute respiratory distress syndrome in the rat," Journal of Pineal Research, 2015, 58: 137-150.
Surma et al., "An automated shotgun lipidomics platform for high throughput, comprehensive, and quantitative analysis of blood plasma intact lipids," European Journal of Lipid Science and Technology, Oct. 2015, 117(10):1540-9.

(56) References Cited

OTHER PUBLICATIONS

Suzuki et al., "In vivo porcine model of reperfused myocardial infarction: in situ double staining to measure precise infarct area/area at risk," Catheterization and Cardiovascular Interventions, Jan. 1, 2008, 71(1):100-7.
Templeton et al., "Improved DNA: liposome complexes for increased systemic delivery and gene expression," Nature Biotechnology, Jul. 1997, 15(7):647-52.
Thuwanut et al., "Cryopreservation of epididymal cat spermatozoa: effects of in vitro antioxidative enzymes supplementation and lipid peroxidation induction," Theriogenology, May 1, 2010, 73(8):1076-87.
Titov et al., "Complementation of mitochondrial electron transport chain by manipulation of the NAD+/NADH ratio," Science, Apr. 8, 2016, 352(6282):231-5.
Tonelli et al., "Causes and circumstances of death in pulmonary arterial hypertension," American Journal of Respiratory and Critical Care Medicine, Aug. 1, 2013, 188(3):365-9.
Toyoda et al., "Opening of Mitochondrial ATP-Sensitive Potassium Channels Enhances Cardioplegic Protection," Ann Thorac Surg, Apr. 2001, 71: 1281-9.
Treulen et al., "Cryopreservation induces mitochondrial permeability transition in a bovine sperm model," Cryobiology, Aug. 2018, 83:65-74.
Trudeau et al., "Lysosome acidification by photoactivated nanoparticles restores autophagy under lipotoxicity," Journal of Cell Biology, Jul. 4, 2016, 214(1):25-34.
Tsukube et al., Amelioration of ischemic calcium overload correlates with high-energy phosphates in senescent myocardium, Am J Physiol Heart Cir Physiol, Jul. 1997, 273: H418-H425.
Tsukube et al., "Developmental Differences in Cytosolic Calcium Accumulation Associated With Surgically Induced Global Ischemia: Optimization of Cardioplegic Protection and Mechanism of Action," The Journal of Thoracic and cardiovascular Surgery, Jul. 1996, 112: 175-184.
Uchenna Agu et al., "The lung as a route for systemic delivery of therapeutic proteins and peptides," Respiratory Research, Aug. 2001, 2(4):1-2.
Ui-Tei et al., "Sensitive assay of RNA interference in *Drosophila* and Chinese hamster cultured cells using firefly luciferase gene as target," FEBS Letters, Aug. 18, 2000, 479(3):79-82.
Vander Heiden et al. "Bcl-xL Regulates the Membrane Potential and Volume Homeostasis of Mitochondria" Cell, Nov. 28, 1997, 91(5):627-37.
Vander Heiden et al., "Understanding the Warburg Effect: The Metabolic Requirements of Cell Proliferation," Science, May 2009, 324: 1029-1033.
Varkouhi et al., "Endosomal escape pathways for delivery of biologicals," Journal of Controlled Release, May 2011, 151(3):220-8.
Vlieghe et al., "Synthetic therapeutic peptides: science and market," Drug Discovery Today, Jan. 1, 2010, 15(1-2):40-56.
Wakiyama et al., "Selective opening of mitochondrial ATP-sensitive potassium channels during surgically induced myocardial ischemia decreases necrosis and apoptosis," European Journal of Cardio-Thoracic Surgery, Mar. 1, 2002, 21(3):424-33.
Walter et al., "Advanced tools for the analysis of protein phosphorylation in yeast mitochondria," Analytical Biochemistry, Aug. 1, 2018, 554:23-7.
Wang et al., "Correcting human mitochondrial mutations with targeted RNA import," Proceedings of the National Academy of Sciences, Mar. 27, 2012, 109(13):4840-5.
Weber-Lotfi et al., "DNA import competence and mitochondrial genetics," Biopolymers and Cell, Jan. 2014(30)1:71-3.
Weber-Lotfi et al., "Nucleic acid import into mitochondria: new insights into the translocation pathways," Biochimica et Biophysica Acta (BBA)—Molecular Cell Research, Dec. 1, 2015, 1853(12):3165, 43 pages.
Wibom et al., "Measurement of ATP production and respiratory chain enzyme activities in mitochondria isolated from small muscle biopsy samples," Analytical Biochemistry, Dec. 15, 2002, 311(2):139-51.
Wieckowski et al., "Isolation of mitochondria-associated membranes and mitochondria from animal tissues and cells," Nat Protoc, Nov. 2009, 4:1582-1590.
Wright, "A new nebuliser," The Lancet, Jul. 1958, 272(7036):24-5.
Wu et al., "Covalent labeling of mitochondria with a photostable fluorescent thiol-reactive rhodamine-based probe," Analytical Methods, Mar. 2012, 4(6):1699-703.
Wu et al., "MicroRNAs direct rapid deadenylation of mRNA," Proceedings of the National Academy of Sciences, Mar. 14, 2006, 103(11):4034-9.
Yamaguchi et al., "Mitochondria frozen with trehalose retain a number of biological functions and preserve outer membrane integrity" Cell Death and Differentiation, 14:616-624, 2007.
Yin et al., "Adipocyte mitochondrial function is reduced in human obesity independent of fat cell size," The Journal of Clinical Endocrinology & Metabolism, Feb. 1, 2014, 99(2):E209-16.
Yin et al., "Non-viral vectors for gene-based therapy," Nature Reviews Genetics, Aug. 2014, 15(8):541-55.
Yu et al., "Capitalizing Resolving Power of Density Gradient Ultracentrifugation by Freezing and Precisely Slicing Centrifuged Solution: Enabling Identification of Complex Proteins from Mitochondria by Matrix Assisted Laser Desorption/Ionization Time-of-Flight Mass Spectrometry," Journal of Analytical Methods in Chemistry, 2016:1-7, 2016.
Yu et al., "Gene delivery to mitochondria by targeting modified adenoassociated virus suppresses Leber's hereditary optic neuropathy in a mouse model," Proceedings of the National Academy of Sciences, May 15, 2012, 109(20):E1238-47.
Yu et al., "Interaction between bevacizumab and murine VEGF-A: a reassessment," Investigative Ophthalmology & Visual Science, Feb. 2008, 49(2):522-7.
Zamzamiet et al., "Mitochondrial permeability transition in apoptosis and necrosis," Cell Death and Differentiation, Nov. 1, 2005, 12(S2):1478.
Zeng et al., "Both natural and designed micro RNAs can inhibit the expression of cognate mRNAs when expressed in human cells," Molecular Cell, Jun. 1, 2002, 9(6):1327-33.
Zetsche et al. "Cpf1 is a single RNA-guided endonuclease of a class 2 CRISPR-Cas system," Cell, Oct. 2015, 163:759-771.
Zhao et al., "Glutathione selectively modulates the binding of platinum drugs to human copper chaperone Cox17," Biochem J, Dec. 2015, 472(2):217-23.
Zhou et al., "Progress in the Field of Constructing Near-Infrared Light-Responsive Drug Delivery Platforms," Journal of Nanoscience and Nanotechnology, Mar. 2016, 16: 2111-2125.
AU Office Action in Australian Appln. No. 2023200521, mailed on Feb. 9, 2024, 3 pages.
CA Office Action in Canadian Appln. No. 2,952,121, mailed on Oct. 31, 2023, 5 pages.
CA Office Action in Canadian Appln. No. 3,011,472, mailed on Aug. 29, 2023, 5 pages.
CA Office Action in Canadian Appln. No. 3,130,213, mailed on Nov. 2, 2023, 4 pages.
CN Office Action in Chinese Appln. No. 202080039304.2, mailed on Feb. 19, 2024, 12 pages (with English translation).
Deuse et al., "SCNT-derived ESCs with mismatched mitochondria trigger an immune response in allogeneic hosts," Cell Stem Cell, Jan. 2015, 16(1):33-8.
EP Extended European Search Report in European Appln. No. 23179249.0, mailed on Nov. 30, 2023, 10 pages.
EP Office Action in European Appln. No. 20756733.0, mailed on Dec. 5, 2023, 10 pages.
EP Office Action in European Appln. No. 20790601.7, mailed on Oct. 11, 2023, 3 pages.
Hosseinian et al., "Prospects of mitochondrial transplantation in clinical medicine: Aspirations and challenges," Mitochondrion, Jul. 2022, 65:33-44.
JP Office Action in Japanese Appln. No. 2021-547460, mailed on Dec. 22, 2023, 10 pages (with English translation).

(56) References Cited

OTHER PUBLICATIONS

JP Office Action in Japanese Appln. No. 2022188165, mailed on Oct. 23, 2023, 8 pages (with English translation).
Kholmukhamedov et al., "Mitotracker probes and mitochondrial membrane potential," Shock, Jun. 2013, 39(6):543, 2 pages.
Kompas.com, "Dilated Cardiomyopathy," Keio University Hospital KOMPAS, Jan. 26, 2018, retrieved Jan. 17, 2024 from URL <https://kompas.hosp.keio.ac.jp/contents/000200.html>, 5 pages (with English translation).
Medicalnote.jp, "About Pulmonary Heart Disease," Sep. 11, 2018, retrieved Dec. 12, 2023 from URL <https://medicalnote.jp/diseases/肺性心>, 3 pages (English translation).
Piao et al., "Mitochondrial metabolic adaptation in right ventricular hypertrophy and failure," Journal of Molecular Medicine, Oct. 2010, 88:1011-20.
RU Office Action in Russian Appln. No. 2021126922, mailed on Nov. 14, 2023, 14 pages (with English translation).
Tohoku.jp, "Elucidating the Mechanism of Pulmonary Hypertension Associated with Left Heart Failure—Identification of a Novel Drug Candidate for Heart Failure," Press Release, Graduate School of Medicine, Tohoku University, Jul. 10, 2018, retrieved Jan. 17, 2024 from URL <https://www.tohoku.ac.jp/japanese/newimg/pressimg/tohokuuniv-press20180710_Shimokawa180703_01web.pdf>, 12 pages (with English translation).
Twmu.jp, "Cardiac Enlargement and Cardiac Hypertrophy," Column, Adult Medical Center, Tokyo Women's Medical University, Jun. 1, 2012, retrieved Jan. 17, 2024 from URL <http://www.twmu.ac.jp/IOG/column/file32.html>, 3 pages (English translation).
Weixler et al., "Autogenous mitochondria transplantation for treatment of right heart failure," The Journal of Thoracic and Cardiovascular Surgery, Jul. 2021, 162(1):e111-21.
AU Office Action in Australian Appln. No. 2023200521, mailed on Oct. 10, 2024, 3 pages.
CN Office Action in Chinese Appln. No. 201780013452.5, dated Jun. 21, 2023, 16 pages (with English translation).
JP Japanese Office Action in Japanese Appln. No. 2020-173126, dated Jul. 12, 2023, 5 pages (with English translation).
AU Office Action in Australian Appln. No. 2021201217, dated Jan. 18, 2023, 4 pages.
CA Office Action in Canadian Appln. No. 3,011,472, dated Jan. 12, 2023, 5 pages.
CN Office Action in Chinese Appln. No. 201780013452.5, dated Jan. 31, 2023, 13 pages (with English translation).
CN Office Action in Chinese Appln. No. 2022111501695770, dated Nov. 18, 2022, 19 pages (with English translation).
EP Extended Search Report in European Appln. No. 19926810.3, dated Jan. 5, 2023, 11 pages.
EP Extended Search Report in European Appln. No. 20790601.7, dated Feb. 17, 2023, 10 pages.
EP Office Action in European Appln. No. 20155650.3, dated Dec. 6, 2022, 4 pages.
CA Office Action in Canadian Appln. No. 2952121, mailed on Jun. 17, 2025, 6 pages.
AU Office Action in Australian Appln. No. 2025200879, mailed on Apr. 8, 2026, 2 pages.

* cited by examiner

| | 1 | 2 | 3 | 4 | 5 | 6 | 7 | 8 | 9 | 10 | 11 | 12 |
|---|---|---|---|---|---|---|---|---|---|---|---|---|
| A | 0.1 mM ATP standard (10 µL) | 0.1 mM ATP standard (10 µL) | 0.05 mM ATP standard (10 µL) | 0.05 mM ATP standard (10 µL) | 0.01 mM ATP standard (10 µL) | 0.01 mM ATP standard (10 µL) | 0.005 mM ATP standard (10 µL) | 0.005 mM ATP standard (10 µL) | 0.001 mM ATP standard (10 µL) | 0.001 mM ATP standard (10 µL) | 0.0001 mM ATP standard (10 µL) | 0.0001 mM ATP standard (10 µL) |
| B | Mito Sample 1 (10 µL) | Mito Sample 1 (10 µL) | Mito Sample 1 (10 µL) | Mito Sample 2 (10 µL) | Mito Sample 2 (10 µL) | Mito Sample 2 (10 µL) | Mito Sample 3 (10 µL) | Mito Sample 3 (10 µL) | Mito Sample 3 (10 µL) | Mito Sample 4 (10 µL) | Mito Sample 4 (10 µL) | Mito Sample 4 (10 µL) |
| C | Mito Sample 5 (10 µL) | Mito Sample 5 (10 µL) | Mito Sample 5 (10 µL) | Mito Sample 6 (10 µL) | Mito Sample 6 (10 µL) | Mito Sample 6 (10 µL) | Respiration Buffer (10 µL) | Respiration Buffer (10 µL) | Respiration Buffer (10 µL) | | | |

FIG. 5

PRODUCTS AND METHODS TO ISOLATE MITOCHONDRIA

CROSS-REFERENCE TO RELATED APPLICATIONS

This application is a 371 U.S. National Phase Application of PCT/US2015/035584, filed on Jun. 12, 2015, which claims the benefit of U.S. Application No. 62/012,045, filed on Jun. 13, 2014, all of which are incorporated by reference herein.

FEDERALLY SPONSORED RESEARCH OR DEVELOPMENT

This invention was made with government support under Grant Number HL103642 awarded by the National Institutes of Health. The government has certain rights in the invention.

TECHNICAL FIELD

This invention relates to filtration apparatuses, kits, and methods to isolate intact, viable mitochondria that may be used in a clinical setting.

BACKGROUND

Mitochondria exist in every cell in the body except red blood cells and are involved in a large number of important cellular and metabolic processes (van Loo et al., *Cell Death Differ* 9:1031-1042, 2002; Szabadkai et al., *Physiology* (Bethesda) 23:84-94 doi: 0.1152/physio1.00046.2007, 2008; Chan, *Cell* 125:1241-1252, 2006; Picard et al., *PLoS ONE* 6, e18317, doi: 10.1371/joumal.pone.0018317, 2011). Because of these many functions, mitochondrial damage can have detrimental effects (Chan, *Cell* 125:1241-1252, 2006). To investigate mitochondrial function and dysfunction, several mitochondrial isolation methods have been described. The earliest published accounts of mitochondrial isolation appear to date to the 1940s (Bensley et al., *Anat Rec* 60:449-455, 1934; Claude, *J Exp Med* 84:61-89, 1946; Hogeboom et al., *J Biol Chem* 172:619-635, 1948; Emster et al., *J Cell Biol* 91 (3 Pt 2), 227s-255s, 1981). One attempt demonstrated mitochondrial isolation by grinding liver tissue in a mortar followed by centrifugation in a salt solution at low speed (Bensley et al., *Anat Rec* 60:449-455, 1934; Emster et al., *J Cell Biol* 91 (3 Pt 2), 227s-255s, 1981). Other groups expanded upon the original procedure and demonstrated tissue fractionation based on differential centrifugation (Claude, *J Exp Med* 84:61-89, 1946; Hogeboom et al., *J Biol Chem* 172:619-635, 1948; Emster et al., *J Cell Biol* 91 (3 Pt 2), 227s-255s, 1981). These early methods formed the basis of current art-known techniques, which often incorporate homogenization and/or differential centrifugation (Pallotti et al., *Methods Cell Biol* 80:3-44, 2007; Schmitt et al., *Anal Biochem* 443:66-74, doi: 10.1016/j.ab.2013.08.007, 2013; Fernández-Vizarra et al., *Mitochondrion* 10:253-262, doi: 10.1016/j.mito.2009.12.148, 2010; Graham et al., *Curr Protoc Cell Biol Chapter* 3, Unit 3.3, doi: 10.1002/0471143030.cb0303s04, 2001; Frezza et al., *Nat Protoc* 2:287-295, 2007; Wieckowski et al., *Nat Protoc* 4:1582-1590, doi: 10.1038/nprot.2009.151, 2009; Gostimskaya et al., *J Vis Exp* (43), pii:2202, doi: 10.3791/2202, 2010). The number of homogenization and centrifugation steps varies among protocols. These repetitive steps increase the time for mitochondrial isolation and ultimately reduce viability. In addition, manual homogenization can cause mitochondrial damage and inconsistent results if not properly controlled (Schmitt et al., *Anal Biochem* 443:66-74, doi: 10.1016/j.ab.2013.08.007, 2013; Gross et al., *Anal Biochem* 418:213-223, doi: 10.1016/j.ab.2011.07.017, 2011).

SUMMARY

The present disclosure is based, at least in part, on the discovery that viable, respiration-competent mitochondria can be isolated with high yield and high purity by differential filtration. In particular, applicants have found that a filter with a pore size of about 5 μm to about 20 μm, e.g., about 6 μm, 8 μm, 10 μm, 12 μm, 15 μm, or about 18 μm, allows mitochondria to be collected in a filtrate, while cell debris and other organelles are retained by the filter. Accordingly, the present specification provides, e.g., filtration apparatuses, kits, and methods to isolate viable, respiration-competent mitochondria.

In one aspect, the present disclosure provides filtration apparatuses that can have a tubular body configured to be received in a centrifuge tube and having a lumen and first and second ends, each end having an opening; a first filter disposed and secured within the lumen, wherein the filter has a pore-size of about 30 μm to about 50 μm, e.g., about 33 μm, 35 μm, 38 μm, 40 μm, 42 μm, 45 μm, or about 48 μm; and a second filter disposed and secured within the lumen adjacent to the first filter and having a pore-size of about 5 μm to about 20 μm, e.g., about 6 μm, 8 μm, 10 μm, 12 μm, 15 μm, or about 18 μm. In some embodiments, the filtration apparatuses can have a third filter disposed and secured within the lumen adjacent to the first filter and the second filter and having a pore-size of about 15 μm to about 50 μm, e.g., about 18 μm, 20 μm, 22 μm, 25 μm, 28 μm, 30 μm, 33 μm, 35 μm, 38 μm, 40 μm, 42 μm, 45 μm, or about 48 μm. In some embodiments, the first filter and the third filter have the same pore-size, e.g., 30 μm, 33 μm, 35 μm, 38 μm, 40 μm, 42 μm, 45 μm, 48 μm, or about 50 μm. In some embodiments, the second filter and the third filter have the same pore-size, e.g., 15 μm, 16 μm, 17 μm, 18 μm, 19 μm, or about 20 μm. In one embodiment, the filtration apparatuses can be sterile. In some embodiments, the first, second, and third filters comprise nylon, mylar, stainless steel, wire mesh, aluminum, synthetic mesh, spectra, Kevlar, plastic, paper, or any combination thereof. In yet another embodiment, the centrifuge tube is a 50 mL centrifuge tube.

In another aspect, the present disclosure provides kits having at least one, e.g., two, three, five, or ten or more, filtration apparatuses described above, e.g., apparatuses that have a tubular body configured to be received in a centrifuge tube and having a lumen and first and second ends, each end having an opening; a first filter disposed and secured within the lumen, wherein the filter has a pore-size of about 30 μm to about 50 μm, e.g., about 33 μm, 35 μm, 38 μm, 40 μm, 42 μm, 45 μm, or about 48 μ.m; and a second filter disposed and secured within the lumen adjacent to the first filter and having a pore-size of about 5 μm to about 20 μm, e.g., about 6 μm, 8 μm, 10 μm, 12 μm, 15 μm, or about 18 μm. In one embodiment, the kit can include a first solution having 300 mM sucrose; 10 mM $K^+$HEPES, pH 7.2; and 1 mM $K^+$EGTA, pH 8.0; a second solution having 2 mg Subtilisin A per 1 mL of the first solution; a third solution having 10 mg BSA per 1 mL of the first solution; a fourth solution having 1 mg BSA per 1 mL of the first solution; a 50 mL centrifuge tube; and a 1.5 mL microcentrifuge tube. In some embodiments, the 50 mL centrifuge tube and the 1.5 mL microcentrifuge tube are sterile.

In yet another aspect, the present disclosure provides methods to isolate viable, respiration-competent mitochondria. The methods can include providing a cell homogenate having a viable mitochondrion; providing a filtration apparatus described above, e.g., an apparatus that has a tubular body configured to be received in a centrifuge tube and having a lumen and first and second ends, each end having an opening; a first filter disposed and secured within the lumen, wherein the filter has a pore-size of about 30 μm to about 50 μm, e.g., about 33 μm, 35 μm, 38 μm, 40 μm, 42 μm, 45 μm, or about 48 μm; and a second filter disposed and secured within the lumen adjacent to the first filter and having a pore-size of about 5 μm to about 20 μm, e.g., about 6 μm, 8 μm, 10 μm, 12 μm, 15 μm, or about 18 μm; optionally, situating the filtration apparatus in a relatively upright position; introducing the cell homogenate into the opening at the first end such that the cell homogenate contacts and is filtered through the first filter and subsequently the second filter to thereby form a filtrate; and collecting the filtrate, thereby isolating the viable mitochondrion.

In one embodiment, the method includes homogenizing a tissue, e.g., mammalian tissue, e.g., mammalian tissue from a tissue biopsy, in a solution comprising 300 mM sucrose; 10 mM $K^+$HEPES, pH 7.2; and 1 mM $K^+$EGTA, pH 8.0, to thereby provide the cell homogenate. In some embodiments, the method can include, prior to introducing the cell homogenate, wetting the second filter with a solution comprising 1 mg BSA in 1 mL of a solution comprising 300 mM sucrose; 10 mM $K^+$HEPES, pH 7.2; and 1 mM $K^+$EGTA, pH 8.0. In one embodiment, the method can include centrifuging the apparatus at about 1×g for three minutes prior to collecting the filtrate. In some embodiments, the filtrate is centrifuged at 9000 rpm at 4° C. for five minutes. In one embodiment, the cell homogenate can be provided by homogenizing tissue in a sterile glass-grinding vessel.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 5 is a table showing a plate map for ATP assay.

DETAILED DESCRIPTION

Previously described mitochondrial isolation methods using differential centrifugation and/or Ficoll gradient centrifugation typically require 60 to 100 minutes to complete. Described herein are filtration apparatuses, kits, and methods for rapid isolation of mitochondria from tissues. Certain methods described herein employ a tissue dissociator and differential filtration. In this method, manual homogenization can be replaced with the tissue dissociator's standardized homogenization cycle, which allows for uniform and consistent homogenization of tissue that is not easily achieved with manual homogenization. Following tissue dissociation, the cell homogenate is filtered through nylon mesh filters, which eliminate repetitive centrifugation steps. As a result, mitochondrial isolation can be performed in less than 30 minutes. A typical isolation using the filtration apparatuses, kits, and methods described herein can yield approximately $2\times10^{10}$ viable and respiration-competent mitochondria from 0.18±0.04 g (wet weight) of tissue sample.

Filtration apparatuses described herein can be used to rapidly isolate intact, viable mitochondria in 30 minutes or less, e.g., 28 minutes, 25 minutes, or 20 minutes or less. Employing differential filtration in place of standard differential centrifugation in methods of isolating mitochondria significantly reduces procedure time and subjects mitochondria to less mechanical stress than using standard differential centrifugation protocols. For example, protocols incorporating several centrifugation steps can take 60 minutes to 100 minutes to isolate mitochondria (Frezza et al., *Nat Protoc* 2:287-295, 2007; Wieckowski et al., *Nat Protoc* 4:1582-1590, doi: 10.1038/nprot.2009.151, 2009; Gostimskaya et al., *J Vis Exp* (43), pii:2202, doi: 10.3791/2202, 2010; Gross et al., *Anal Biochem* 418:213-223, doi: 10.1016/j.ab.2011.07.017, 2011; Masuzawa et al., Amer J Physiol Heart Circ Physiol 304:H966-H982, doi: 10.1152/ajpheart.00883.2012, 2013). Another advantage of the present filtration apparatuses, kits, and isolation methods is that tissue homogenization is standardized. A tissue dissociator provides a standardized cycle and yields consistent and reproducible results. This is in contrast to manual homogenization that is subject to user variability and inconsistency. The isolation time frame provided by the present methods is compatible for clinical and surgical therapeutic intervention (Masuzawa et al., Amer J Physiol Heart Circ Physiol 304: H966-H982, doi: 10.1152/ajpheart.00883.2012, 2013; McCully et al., Amer J Physiol Heart Circ Physiol 296:H94-H105, doi: 10.1152/ajpheart.00567.2008, 2009).

Apparatuses

Figure 1:
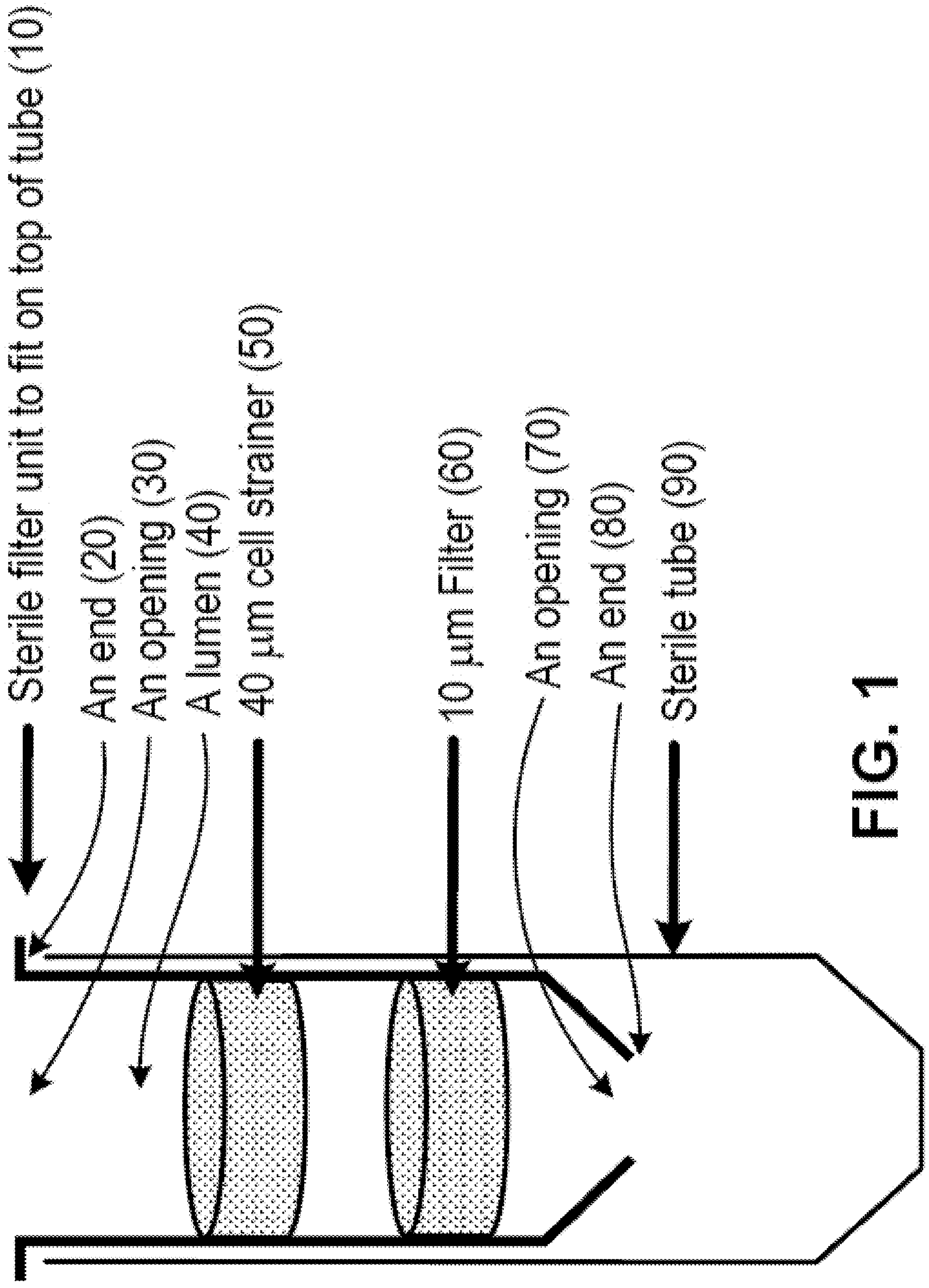
FIG. 1 is a schematic diagram showing an exemplary filtration apparatus.

Filtration apparatuses described herein feature a body (e.g., a tubular body) configured to house multiple filters, which are further described below and represented in FIG. 1. Body (10) can be shaped to fit into a centrifuge tube (90). Body (10) and centrifuge tube (90) can be of any size. Body (10) has first and second ends (20) and (80), each end having an opening (30) and (70). The body has a lumen (40), such that a sample can be placed into the body at one end, travel through lumen (40), and be retrieved at the opposite end, after the sample progresses through at least two filters disposed within the body, e.g., by force of gravity, capillary action, and/or centrifugation. Skilled practitioners will appreciate that one or both ends (20 and/or 80), while each has an opening, can in some embodiments be reversibly capped, e.g., to preserve sterility and/or provide an area to collect filtrate. Typically, the body will have a roughly circular cross-section along the length of the body. However, skilled practitioners will appreciate that the cross-section of the body can be of any shape desired, e.g., oval, square, rectangular, triangular, etc. In some embodiments, the cross-section is roughly circular so that the body can be received within a commercially-available centrifuge tube (90), e.g., a 50 mL centrifuge tube. Skilled practitioners will appreciate that tubular body (10) can be constructed from any art-known material, e.g., polypropylene or polystyrene. One end of the body, e.g., end (80), can have a tapered configuration (shown in FIG. 1) to facilitate insertion of the body into a centrifuge tube and/or to aid in retaining the filter(s) within the body.

The apparatuses include a first filter (50) disposed and secured within the lumen, wherein the filter has a pore-size of about 30 μm to about 50 μm, e.g., about 30 μm, 33 μm, 35 μm, 38 μm, 40 μm, 42 μm, 45 μm, 48 μm, or about 50 μm. The first filter can be constructed from any art-known filter material, e.g., nylon, mylar, stainless steel, wire mesh, aluminum, synthetic mesh, spectra, Kevlar, plastic, paper, or any combination thereof. The apparatuses also include a second filter (60) disposed and secured within the lumen adjacent to the first filter and have a pore-size of about 5 μm to about 20 μm, e.g., about 5 μm, 6 μm, 8 μm, 10 μm, 12 μm, 15 μm, 18 μm, or about 20 μm. The second filter can be constructed from any art-known filter material, e.g., nylon, mylar, stainless steel, wire mesh, aluminum, synthetic mesh, spectra, Kevlar, plastic, paper, or any combination thereof. The first and second filters can be situated within the body such that they contact each other or are spaced apart some distance apart. For example, the first and second filters can be disposed within the body at a distance apart of at least or about 0.5 mm, e.g., at least or about 1 mm, 2 mm, 3 mm, 4 mm, 5 mm, 8 mm, 1 cm, 2 cm, 5 cm, or at least or about 10 cm, depending on the intended use and/or the length of the body.

The apparatuses can optionally include a third filter disposed and secured within the lumen adjacent to the first filter and the second filter and have a pore-size of about 15 μm to about 50 μm, e.g., about 15 μm, 18 μm, 20 μm, 22 μm, 25 μm, 28 μm, 30 μm, 33 μm, 35 μm, 38 μm, 40 μm, 42 μm, 45 μm, 48 μm, or about 50 μ. The third filter can be constructed from any art-known filter material, e.g., nylon, mylar, stainless steel, wire mesh, aluminum, synthetic mesh, spectra, Kevlar, plastic, paper, or any combination thereof. The third filter can be disposed between the first and second filters. In some embodiments, the third filter is disposed between the first filter and first opening, i.e., closer to the first opening than the first filter. In other embodiments, the third filter is disposed between the second filter and the second opening, i.e., closer to the second opening than the second filter. The third filter can be disposed such that it contacts the first filter and/or the second filter, or the three filters can be evenly spaced apart, or unevenly spaced apart. For example, when the third filter is disposed between the first and second filters, the first and third filters can be in contact with each other, or at least or about 0.5 mm apart, e.g., at least or about 1 mm, 2 mm, 3 mm, 4 mm, 5 mm, 8 mm, 1 cm, 2 cm, 5 cm, or at least or about 10 cm apart; and the third and second filters can be in contact with each other, or at least or about 0.5 mm apart, e.g., at least or about 1 mm, 2 mm, 3 mm, 4 mm, 5 mm, 8 mm, 1 cm, 2 cm, 5 cm, or at least or about 10 cm apart.

Skilled practitioners will appreciate that further filters (e.g., a fourth filter, fifth filter, sixth filter, etc.) may in some instances be added, depending on the intended use. In some embodiments, the apparatus is sterile. Skilled practitioners will appreciate that filters can be secured within the body using any art-known method, e.g., using adhesive, a pressure fit, and/or configuring the lumen walls in a way that causes the filters to be retained in the lumen (e.g., by designing lumen walls to have ridges, grooves, or other retentive elements).

Kits

The present disclosure also provides kits featuring the filtration apparatuses described herein to isolate viable mitochondria. Such kits include at least one, e.g., two, three, five, or ten, filtration apparatus described above. The kits can further include one or more solutions useful for performing the mitochondria isolation methods described herein. For example, a kit may include a first solution comprising 300 mM sucrose; 10 mM $K^+$HEPES, pH 7.2; and 1 mM $K^+$EGTA, pH 8.0. Alternatively or in addition, the kit may include a second solution comprising 2 mg Subtilisin A per 1 mL of the first solution. Alternatively or in addition, the kit may include a third solution comprising 10 mg BSA per 1 mL of the first solution. Alternatively or in addition, the kit may include solutions comprising inactive human serum albumin or acetylated human serum albumin. Alternatively or in addition, the kit may include a fourth solution comprising 1 mg BSA per 1 mL of the first solution. In some instances, the kit may include a 50 mL centrifuge tube, into which the filtration apparatus can be fitted. Alternatively or in addition, the kit can include a 1.5 mL microcentrifuge tube. In some embodiments, the 50 mL centrifuge tube and the 1.5 mL microcentrifuge tube are sterile.

Methods of Isolating Mitochondria

In an exemplary method, intact, viable mitochondria are isolated from tissue, e.g., mammalian tissue, e.g., mammalian tissue from a tissue biopsy. For example, tissue from a mammal can be minced, e.g., with a scalpel, and homogenized in a sterile glass-grinding vessel (Thomas, Philadelphia, PA) with a motor-driven pestle for 5 to 10 seconds at 4° C. in a first solution containing 300 mM sucrose; 10 mM $K^+$HEPES, pH 7.2; and 1 mM $K^+$EGTA, pH 8.0. A solution containing 2 mg Subtilisin A per 1 mL of the first solution is then added to the homogenate and incubated on ice for 10 minutes.

After incubation on ice, the cell homogenate is introduced to a sterile filtration apparatus that is positioned relatively upright, as described herein. In some embodiments, a volume of the cell homogenate, e.g., about 100 μL, 200 μL, 300 μL, 400 μL, 500 μL, 600 μL, 700 μL, 800 μL, 900 μL, 1 mL, 1.5 mL, 2 mL, 2.5 mL, 3 mL, 4 mL, 5 mL, 6 mL, 7 mL, 10 mL, 15 mL, 20 mL, 25 mL, 30 mL, 35 mL, 40 mL, 45 mL, or about 50 mL, is introduced into the opening at the first end such that the cell homogenate contacts the first filter prior to contacting the second filter, and a filtrate is collected after passing through both filters, e.g., by gravity or by centrifugation, in a tube, e.g., a centrifuge tube, a vial, a microcentrifuge tube, or a test tube, to isolate the intact, viable, respiration-competent mitochondria. Alternatively or in addition, the filtration apparatus can have a cap on the second end that is able to collect the filtrate, and the cap can be uncapped or unscrewed to collect the filtrate after the filtrate has flowed through the first filter, second filter, and, if present, third filter, by gravity or centrifugation. In some embodiments, a volume of the cell homogenate can be passed through a filter with a pore-size of about 30 µm to about 50 µm, e.g., about 33 µm, 35 µm, 38 µm, 40 µm, 42 µm, 45 µm, or about 48 µm, and optionally, the filtrate passed through another filter with a pore-size of about 15 µm to about 50 µm, e.g., about 18 µm, 20 µm, 22 µm, 25 µm, 28 µm, 30 µm, 33 µm, 35 µm, 38 µm, 40 µm, 42 µm, 45 µm, or about 48 µm, before being passed through a filter with a pore-size of about 5 µm to about 20 µm, e.g., about 6 µm, 8 µm, 10 µm, 12 µm, 15 µm, or about 18 µm.

Prior to introducing the cell homogenate to the filtration apparatus, the filter with a pore-size of about 5 µm to about 20 µm, e.g., about 6 µm, 8 µm, 10 µm, 12 µm, 15 µm, or about 18 µm, can be wetted with a solution comprising 1 mg BSA in 1 mL of a solution comprising 300 mM sucrose; 10 mM $K^+$HEPES, pH 7.2; and 1 mM $K^+$EGTA, pH 8.0. While not always required in the methods described herein, skilled practitioners will appreciate that filtrate collection can be facilitated by centrifuging the apparatus, e.g., at 1×g for three minutes. Skilled practitioners will appreciate that mitochondria can be concentrated by centrifuging the filtrate at 9000 rpm at 4° C. for five minutes.

EXAMPLES

Several general protocols are described below, which may be used in any of the methods described herein and do not limit the scope of the invention described in the claims.

Example 1: Stock Solutions

The following solutions were prepared to isolate intact, viable, respiration-competent mitochondria. To successfully isolate mitochondria using the present methods, all solutions and tissue samples should be kept on ice to preserve mitochondrial viability. Even when maintained on ice, isolated mitochondria will exhibit a decrease in functional activity over time (Olson et al., *J Biol Chem* 242:325-332, 1967). All solutions should be pre-prepared if possible.

1 M K-HEPES Stock Solution (adjust pH to 7.2 with KOH).

0.5 M K-EGTA Stock Solution (adjust pH to 8.0 with KOH).

1 M $KH_2PO_4$ Stock Solution.

1 M $MgCl_2$ Stock Solution.

Homogenizing Buffer (pH 7.2): 300 mM sucrose, 10 mM K-HEPES, and 1 mM K-EGTA. Stored at 4° C.

Respiration Buffer: 250 mM sucrose, 2 mM $KH_2PO_4$, 10 mM $MgCl_2$, 20 mM K-HEPES Buffer (pH 7.2), and 0.5 mM K-EGTA (pH 8.0). Stored at 4° C.

10×PBS Stock Solution: 80 g of NaCl, 2 g of KCl, 14.4 g of $Na_2HPO_4$, and 2.4 g of $KH_2PO_4$ were dissolved in 1 L double distilled $H_2O$ (pH 7.4).

1×PBS was prepared by pipetting 100 mL 10×PBS into 1 L double distilled $H_2O$.

Subtilisin A Stock was prepared by weighing out 4 mg of Subtilisin A into a 1.5 mL microfuge tube. Stored at −20° C. until use.

BSA Stock was prepared by weighing out 20 mg of BSA into a 1.5 mL microfuge tube. Stored at −20° C. until use.

Example 2: Mitochondrial Isolation

Figure 2:
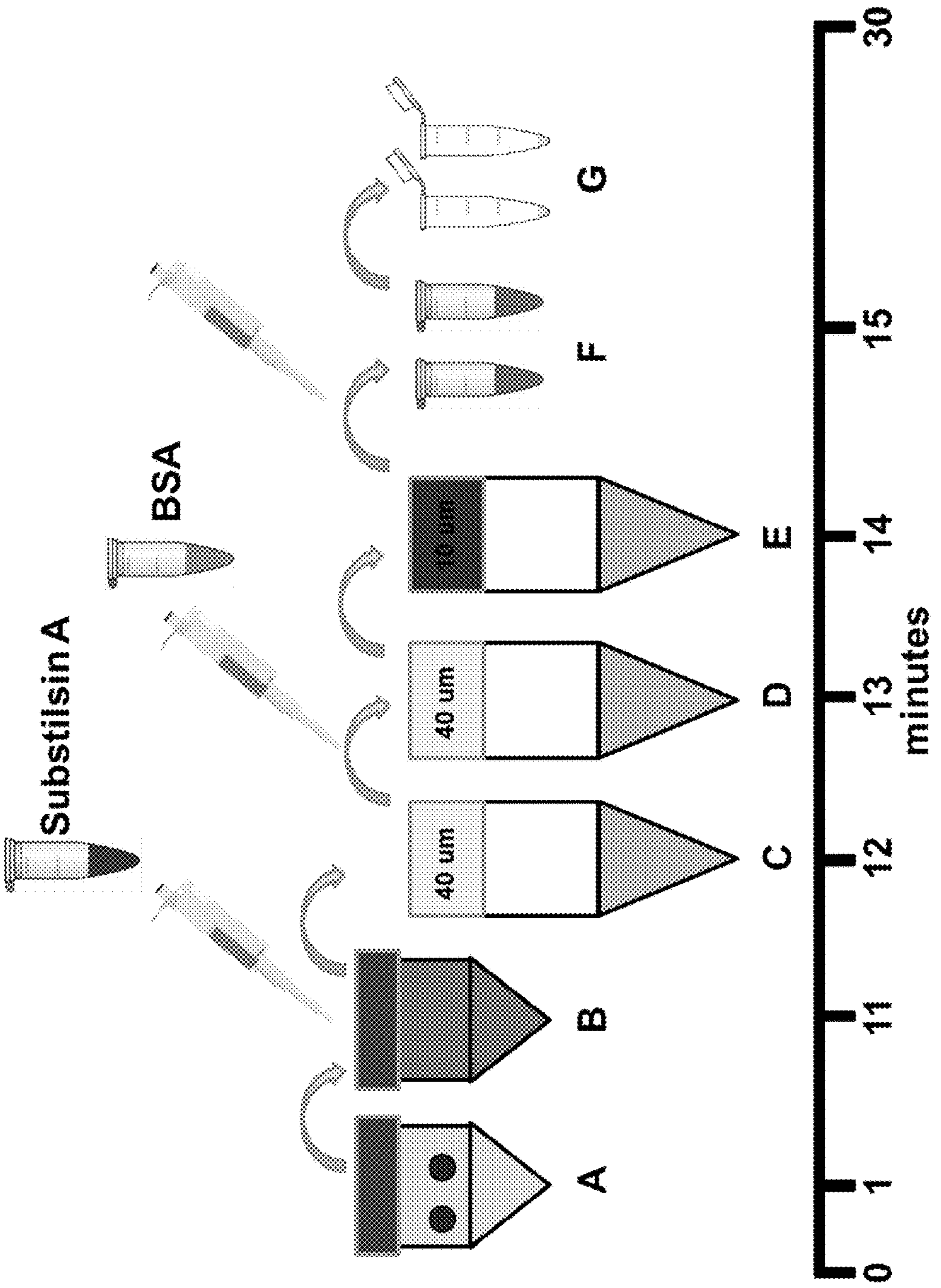
FIG. 2 shows a scheme for isolating mitochondria using tissue dissociation and differential filtration in a total procedure time of less than 30 minutes.

A figure outlining the procedural steps in the isolation of mitochondria using tissue dissociation and differential filtration is shown in FIG. 2. Two, 6 mm biopsy sample punches were transferred to 5 mL of Homogenizing Buffer in a dissociation C tube and the samples were homogenized using the tissue dissociator's 1 minute homogenization program (A). Subtilisin A stock solution (250 µL) was added to the homogenate in the dissociation C tube and incubated on ice for 10 minutes (B). The homogenate was filtered through a pre-wetted 40 µm mesh filter in a 50 mL conical centrifuge tube on ice and then 250 µL of BSA stock solution was added to the filtrate (C). The filtrate was re-filtered through a new pre-wetted 40 µm mesh filter in a 50 mL conical centrifuge on ice (D). The filtrate was re-filtered through a new pre wetted 10 µm mesh filter in a 50 mL conical centrifuge tube on ice (E). The filtrate was transferred to 1.5 mL microfuge tubes and centrifuged at 9000×g for 10 minutes at 4° C. (F). The supernatant was removed, and pellets containing mitochondria were re-suspended, and combined in 1 mL of Respiration Buffer (G).

Immediately prior to isolation, Subtilisin A was dissolved in 1 mL of Homogenizing Buffer. Immediately prior to isolation, BSA was dissolved in 1 mL of Homogenizing Buffer. Two fresh tissue samples were collected using a 6 mm biopsy sample punch and stored in 1×PBS in a 50 mL conical centrifuge tube on ice. The two 6 mm punches of tissue were transferred to a dissociation C tube containing 5 mL of ice cold Homogenizing Buffer. The tissue was homogenized by fitting the dissociation C tube on the tissue dissociator and selecting the pre-set mitochondrial isolation cycle (60 second homogenization).

The dissociation C tube was removed to an ice-bucket. Subtilisin A Stock Solution (250 µL) was added to the homogenate, mixed by inversion, and the homogenate was incubated on ice for ten minutes. A 40 µm mesh filter was placed onto a 50 mL conical centrifuge tube on ice and the filter was pre-wet with Homogenizing Buffer, and the homogenate was filtered into the 50 mL conical centrifuge tube on ice.

Freshly prepared BSA Stock Solution (250 µL) was added to the filtrate and mixed by inversion. (This step was omitted if mitochondrial protein determination was required.) A 40 µm mesh filter was placed onto a 50 mL conical centrifuge tube on ice and the filter was pre-wet with Homogenizing Buffer, and the homogenate was filtered into the 50 mL conical centrifuge tube on ice. A 10 µ.m filter was placed onto the 50 mL conical centrifuge tube on ice, and the filter was pre-wetted with Homogenizing Buffer, and the homogenate was filtered into the 50 mL conical centrifuge tube on ice. The filtrate was transferred to two pre-chilled 1.5 mL microfuge tubes and centrifuge at 9000×g for 10 minutes at 4° C. The supernatant was removed, and the pellets were re-suspended and combined in 1 mL of ice-cold Respiration Buffer.

Example 3: ATP Assay

To determine the metabolic activity of isolated mitochondria, an ATP luminescence assay was performed using an ATP assay kit. The protocol, reagents and standards were supplied in the assay kit. A summary of the procedure is described below.

Kit reagents were equilibrated to room temperature. 10 mM ATP Stock Solution was prepared by dissolving lyophilized ATP pellet in 1,170 μL of double distilled water. ATP standard Stock Solution and prepared mitochondrial samples were stored on ice.

Substrate Buffer solution (5 mL) was added to a vial of lyophilized substrate solution, mixed gently, and placed in the dark. Respiration Buffer (100 μL) was added to all wells of a black, opaque bottom, 96 well plate. Mitochondria from the prepared samples (10 μL) were added to each well of the 96 well plate. Samples were plated in triplicate, and a row for standards and three wells for the negative control (Respiration Buffer) were included. Mammalian cell lysis solution (50 μL) was added to all wells, including standards and controls. The 96 well plate was incubated at 37° C. for 5 minutes on an orbital shaker at 125 rpm. During the incubation, ATP standards were prepared in concentrations of 0.1 mM, 0.05 mM, 0.01 mM, 0.005 mM, 0.001 mM, and 0.0001 mM ATP from the 10 mM ATP Stock Solution and stored on ice. Following the incubation, 10 μL of ATP standards were add to corresponding wells as indicated on the plate map (FIG. 5). This plate map illustrates how to set up standards (A1-Al2), mitochondria samples (B1-C6), and negative controls (C7-C9) for the ATP assay. During the assay, 100 μL of Respiration Buffer, 50 μL of mammalian cell lysis solution, and 50 μL of reconstituted substrate solution are added to all wells (A1-C9). The reconstituted substrate solution (50 μL) was added to each well, and the 96 well plate was incubated at 37° C. on the orbital shaker for 5 minutes at 125 rpm.

The plate was read with a spectrophotometer controlled by Open GenS 1.11 software. Higher values correlate with increased ATP levels and higher metabolic activity.

Example 4: Representative Results

Figure 3:
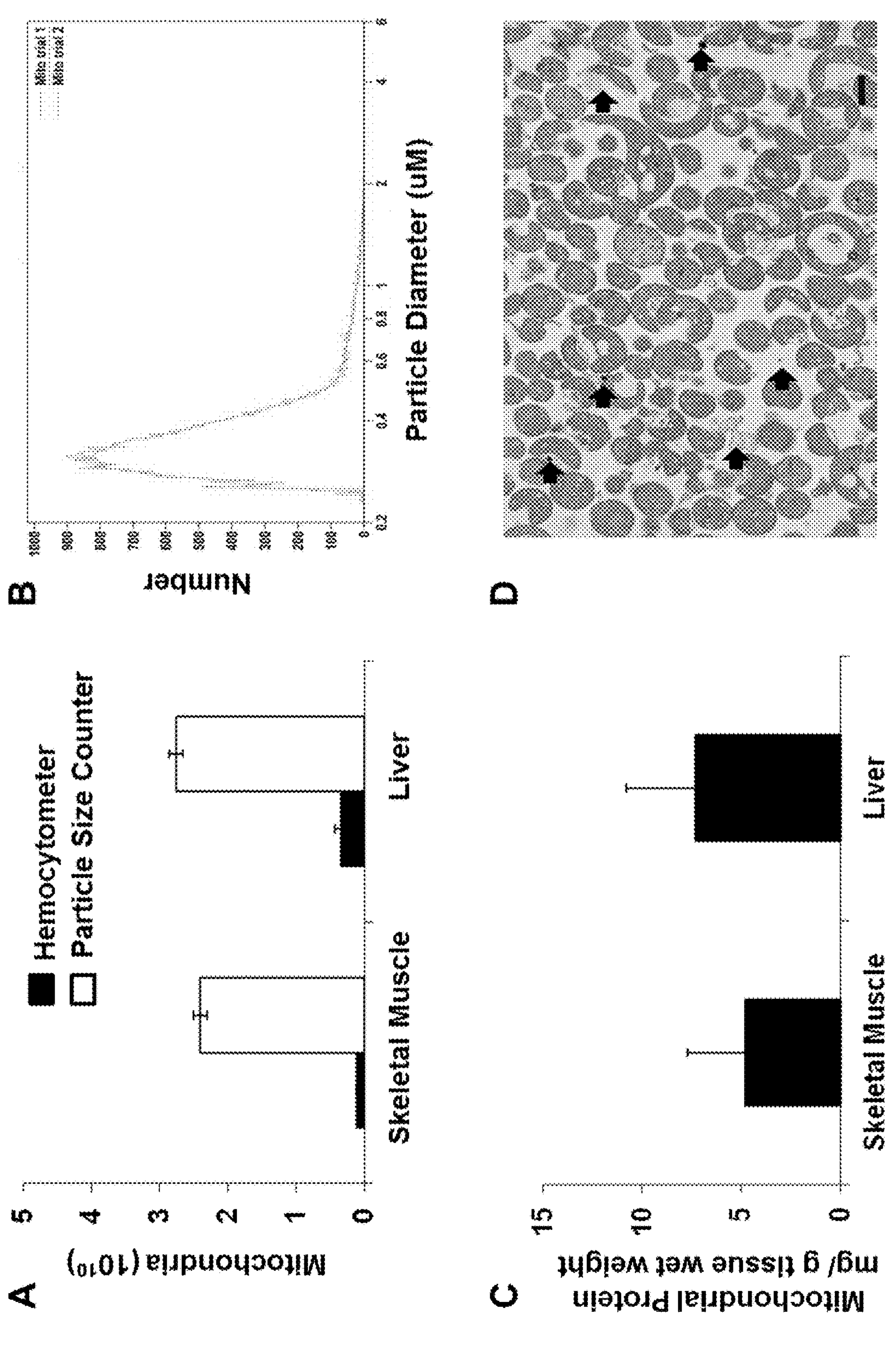
FIG. 3A is a bar graph showing hemocytometer and particle size counter mitochondria number isolated from 0.18±0.04 g tissue (wet weight) for skeletal muscle and liver.
FIG. 3B is a line graph showing mitochondrial size distribution as detected by particle size counter.
FIG. 3C is a bar graph showing mitochondrial protein (mg/g) tissue wet weight for skeletal muscle and liver.
FIG. 3D is a transmission electron microscopy image of isolated mitochondria. Scale bar is 100 nm. Arrows indicate possible contamination by non-mitochondrial particles and damaged mitochondria.

Tissue samples were obtained using a 6 mm biopsy punch. Tissue weight was 0.18±0.04 g (wet weight). The number of mitochondria isolated as determined by particle size counting was $2.4\times10^{10}\pm0.1\times10^{10}$ mitochondria for skeletal muscle and $2.75\times10^{10}\pm0.1\times10^{10}$ mitochondria for liver preparations (FIG. 3A). To allow for comparison, mitochondrial number was also determined by hemocytometer. Mitochondrial numbers were underestimated as determined by hemocytometer as $0.11\times10^{10}\pm0.04\times10^{10}$ mitochondria for skeletal muscle and $0.34\times10^{10}\pm0.09\times10^{10}$ mitochondria for liver preparations (FIG. 3A). Mitochondrial diameter as determined by size based particle counter is shown in FIG. 3B. The representative tracing shows the isolated mitochondria are localized under one peak with mean diameter of 0.38±0.17 μm in agreement with previous reports (Hogeboom et al., *J Biol Chem* 172:619-635, 1948).

Mitochondrial protein/g (wet weight) starting tissue, as determined by Bicinchoninic Acid (BCA) assay, was 4.8±2.9 mg/g (wet weight) and 7.3±3.5 mg/g (wet weight) for skeletal muscle and liver samples respectively (FIG. 3C).

Mitochondrial purity was determined by transmission electron microscopy and is shown in FIG. 3D. Mitochondria are shown to be electron dense with less than 0.01% being fractured or damaged. Contamination by non-mitochondrial particles is less than 0.001%.

Figure 4:
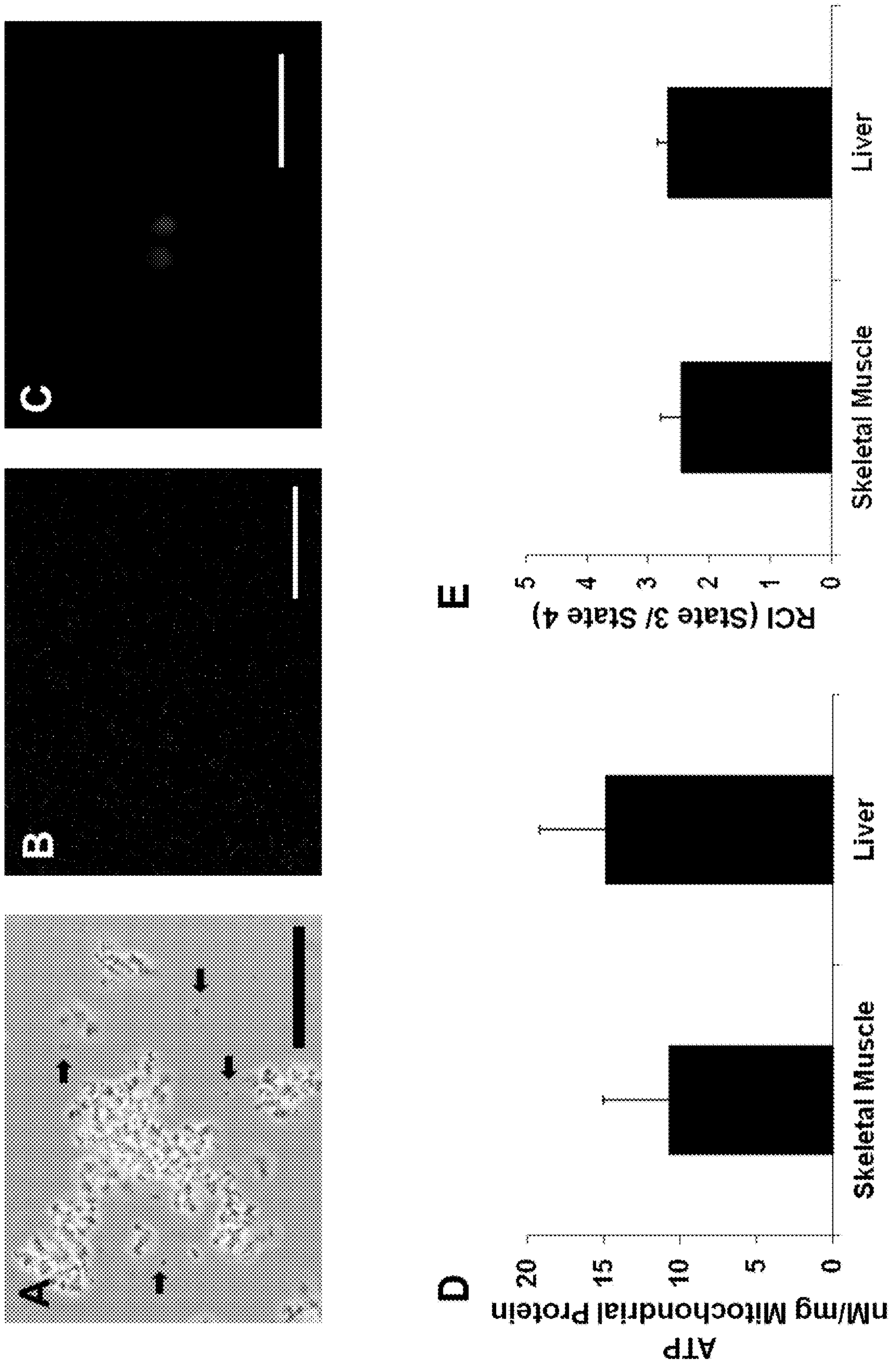
FIG. 4A is a photomicrograph of isolated mitochondria under phase contrast illumination. Scale bar is 25 μm.
FIGS. 4B and 4C are photomicrographs of isolated mitochondria under fluorescence illumination, with mitochondria labeled with MitoTracker Red CMXRos. Scale bars are 25 μm (FIG. 4B) and 5 μm (FIG. 4C).
FIG. 4D is a bar graph depicting ATP content nmol/mg mitochondrial protein as determined by ATP assay.
FIG. 4E is a bar graph showing Respiratory Control Index (RCI) (state 3/state 4) as determined by Clark electrode.

Mitochondrial viability was determined by MitoTracker Red as previously described (Masuzawa et al., Amer J Physiol Heart Circ Physiol 304:H966-H982, doi: 10.1152/ajpheart.00883.2012, 2013; McCully et al., Amer J Physiol Heart Circ Physiol 296:H94-H105, doi: 10.1152/ajpheart.00567.2008, 2009). The present methods produce isolated mitochondria that maintain membrane potential (FIGS. 4A-C). These images indicate that mitochondria maintained membrane potential. Arrows indicate mitochondria lacking membrane potential or debris (FIG. 4A).

ATP was determined using a luminescent assay kit. A plate map for the ATP assay is shown in FIG. 5. ATP standards were plated in duplicate. Mitochondrial samples and negative controls were plated in triplicate. ATP content was 10.67±4.38 nmol/mg mitochondrial protein and 14.83±4.36 nmol/mg mitochondrial protein for skeletal muscle and liver samples, respectively (FIG. 4D).

Mitochondrial respiration was assessed using a Clark type electrode as previously described (Masuzawa et al., Amer J Physiol Heart Circ Physiol 304:H966-H982, doi: 10.1152/ajpheart.00883.2012, 2013; McCully et al., Amer J Physiol Heart Circ Physiol 296:H94-H105, doi: 10.1152/ajpheart.00567.2008, 2009). Mitochondrial oxygen consumption rate was 178±17 nM 02/min/mg mitochondrial protein for skeletal muscle and 176±23 nM $O_2$/min/mg mitochondrial protein for liver preparations. Respiratory control index (RCI) values were 2.45±0.34 and 2.67±0.17 for skeletal muscle and liver sample preparations, respectively (FIG. 4E). These results are similar to those reported in previous studies using manual homogenization and differential centrifugation to isolate mitochondria (Masuzawa et al., Amer J Physiol Heart Circ Physiol 304:H966-H982, doi: 10.1152/ajpheart.00883.2012, 2013; McCully et al., Amer J Physiol Heart Circ Physiol 296:H94-H105, doi: 10.1152/ajpheart.00567.2008, 2009).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for isolating a viable mitochondrion, the method comprising:
- providing a cell homogenate comprising a viable mitochondrion;
- passing the cell homogenate through a first filter having a pore-size of about 30 μm to about 50 μm; and
- subsequently passing the cell homogenate through a second filter having a pore-size of about 5 μm to about 20 μm, thereby isolating the viable mitochondrion,
- wherein the viable mitochondrion is isolated by passing the cell homogenate through the first and the second filters.

2. The method of claim 1, wherein the method comprises passing the cell homogenate through a third filter after the first filter and before the second filter, wherein the third filter has a pore-size of about 15 μm to about 50 μm.

3. The method of claim 1, wherein the method comprises homogenizing a tissue in a solution comprising 300 mM sucrose; 10 mM K HEPES, pH 7.2; and 1 mM K'EGTA, pH 8.0, to thereby provide the cell homogenate.

4. The method of claim 1, wherein the method comprises, prior to introducing the cell homogenate, wetting the second filter with a solution comprising 1 mg BSA in 1 mL of a solution comprising 300 mM sucrose; 10 mM K HEPES, pH 7.2; and 1 mM K+EGTA, pH 8.0.

5. The method of claim 1, further comprising collecting a filtrate, wherein the filtrate is centrifuged at 9000 rpm at 4° C. for five minutes.

6. The method of claim 1, wherein the cell homogenate is provided by homogenizing tissue in a sterile glass-grinding vessel.

7. A method for isolating a viable mitochondrion, the method comprising:

providing a cell homogenate comprising a viable mitochondrion;

passing the cell homogenate through an apparatus comprising:

a tubular body comprising a lumen;

a first filter disposed and secured within the lumen, wherein the filter has a pore-size of about 30 μm to about 50 μm; and a second filter disposed and secured within the lumen adjacent to the first filter and having a pore-size of about 5 μm to about 20 μm, thereby isolating the viable mitochondrion, wherein the viable mitochondrion is isolated by passing the cell homogenate through the first and the second filters.

* * * * *